(12) United States Patent
Petzelt

(10) Patent No.: US 7,271,242 B2
(45) Date of Patent: Sep. 18, 2007

(54) CYTOTOXIC CYPLASIN OF THE SEA HARE, APLYSIA PUNCTATA, CDNA CLONING AND EXPRESSION OF BIOREACTIVE RECOMBINANTS

(75) Inventor: Christian Petzelt, Berlin (DE)

(73) Assignee: Cyplasin Biomedical, Ltd., Edmonton (CA)

( * ) Notice: Subject to any disclaimer, the term of this patent is extended or adjusted under 35 U.S.C. 154(b) by 323 days.

(21) Appl. No.: 10/501,098

(22) PCT Filed: Dec. 18, 2002

(86) PCT No.: PCT/EP02/14511

§ 371 (c)(1),
(2), (4) Date: Dec. 6, 2004

(87) PCT Pub. No.: WO03/057726

PCT Pub. Date: Jul. 17, 2003

(65) Prior Publication Data

US 2005/0277763 A1    Dec. 15, 2005

(30) Foreign Application Priority Data

Jan. 7, 2002 (EP) .................................. 02000388
Sep. 4, 2002 (EP) .................................. 02019914

(51) Int. Cl.
*C07K 14/00* (2006.01)
*C07H 21/04* (2006.01)
(52) U.S. Cl. ...................... 530/350; 930/10; 536/23.1; 530/857
(58) Field of Classification Search ................ 530/350, 530/857; 930/10
See application file for complete search history.

(56) References Cited

OTHER PUBLICATIONS

Takamatsu et al. Molecular Cloning of the Defense Factor in the Albumen Gland of the Sea Hare *Aplysia kurodai*. FEBS Lett. 1995. vol. 377, pp. 373-376.*
Edmondson et al. Structure and Mechanism of Monoamine Oxidase. Current Medicinal Chemistry. 2004. vol. 11, pp. 1983-1993.*
Bowie et al., Deciphering the Message in Protein Sequences: Tolerance to Amino Acid Substitutions. Science. 1990. vol. 247, pp. 1306-1310.*
Wells, J.A., Additivity of Mutational Effects in Proteins. Biochemistry. 1990, vol. 29, No. 37, pp. 8509-8517.*
Kamiya et al. Aplysianin-A, an Antibacterial and Antineoplastic Glycoprotein in the Albumen Gland of a Sea Hare, *Aplysia kurodai*. Experientia. 1986. Vo. 42, pp. 1065-1067.*
Appendix A—Sequence alignment of SEQ ID No. 1 (20-558) and Takamatsu et al. No date.*
Yamazaki, M., Antitumor and antimicrobial glycoproteins from sea hares. Comp. Biochem. Physiol C. Jun. 1993 vol. 105, No. 2, pp. 141-146.*
Appendix B—Sequence alignment of SEQ ID No. 1 to Petzelt AJ304802. No date.*
Petzelt, C.P. "*Aplysia punctata*, mRNA for cyplasin L (ek431 gene)" Database accession No. AJ304802, XP002240886, cited in application, Dec. 21, 2000.
Petzelt, et al., "Cyplasin kills preferentially autonomous cycling cells", Cell Biology International, Academic Press, GB, vol. 25, No. 2, 2001, p. A23, XP001002719, ISSN: 1065-6995, asbtract.
Suzuki, et al., "Lethal effect of the expression of a killer gene SMK1in *Saccharomyces cerevisiae*", Protein Engineering, England Feb. 2000, vol. 13 No. 2 pp. 73-76, XP002240884, ISSN: 0269-2139, p. 74, left-hand column, paragraph 3.
Petzelt, et al., "Cyplasin Cyplasin of the Sea Hare, *Aplysia punctata*, cDNA Cloning, and Expression of Bioreactive Recombinants in Insect Cells", Neoplasia (New York), vol. 4, No. 1, Jan. 2002 pp. 4-59, XP002240885, ISSN: 1522-8002, the whole document.

* cited by examiner

*Primary Examiner*—Kathleen Kerr Bragdon
*Assistant Examiner*—Suzanne M. Noakes
(74) *Attorney, Agent, or Firm*—Steven J. Hultquist; Kelly K. Reynolds; Intellectual Property/Technology Law

(57) ABSTRACT

Described is a nucleic acid coding for a protein called "cyplasin" that shows a preferential toxicity to autonomously growing mammalian cells. Cell death induced by this protein differs from both apoptosis and necrosis. An intracellular cell death which occurs when recombinantly preparing cyplasin in cell cultures can be avoided by removal of the secretion signal in the cyplasin sequence. This modification makes it possible to express the cyplasin in a mammalian cell culture which is preferable with regard to the glycosylation pattern of the obtained protein. Thus, the present invention also relates to a method of recombinantly producing a protein in eukaryotic cells, preferably mammalian cells, which is cytotoxic for said cells when applied externally.

5 Claims, 13 Drawing Sheets

```
            1         10        20        30        40
            +         +         +         +         +
            (L)
         MAVRFLAPGLLTLATLVSGRTVCESKQECDAAQCDKTLDV     L
         ||||||||||||||||||||||||||||||||||||||||
         MAVRFLAPGLLTLATLVSGRTVCESKQECDAAQCDKTLDV     S (T)       (E)
         AIVGAGAAGAYSAYLLRNKGQNIGVFEFCDRVGGRLFTYQ     L
         ||||||||||||||||||||||||||||||||||||||||
         AIVGAGAAGAYSAYLLRNKGQNIGVFEFCDRVGGRLFTYQ     S (H)
         LPNTPDVQLELGGMRYITGAHNLLEGVVRQLGLTPVVFTE     L
         ||||||||||||||||||||||||||||||||||||||||
         LPNTPDVQLELGGMRYITGAHNLLEGVVRQLGLTPVVFTE     S

GFGKLGRTRYYLRGQSLTFQEVLTGDVPYNLTVAEKQNQD     L
         ||||||||||||*|||||||||*|||||||||||||||||
         GFGKLGRTRYYPRGQSLTFQEALTGDVPYNLTVAEKQNQD     S

NIFAFYLKELTRFDVGDGFVTREQLLKLRVSDGRLLYQLT     L
         |||||||||||||||||||||||||||*||||*|||||||
         NIFAFYLKELTRFDVGDGFVTREQLLKLRASDGRPLYQLT     S

FDEALDLVASPEGKEFARDIHVFTTEVSDDANAVSVFDDH     L
         ||||||||||||||||||||||||||||||||||||||||
         FDEALDLVASPEGKEFARDIHVFTTEVSDDANAVSVFDDH     S (L)
         LGEDGVGEEIHTVQEGMQKVPEQLLRAFGNSSVFGHRVFT     L
         |||||||||||||||||||||*||||||||||||||||||
         LGEDGVGEEIHTVQEGMQKVPEQPLRAFGNSSVFGHRVFT     S

NLQLKAIRSKSDKSHVLYFRTTSTVDGKTTILKFEPLQKV     L
         |||||||*|||||||*|||*||||||||||||||||||||
         NLQLKAIRAKSDKSHVPYFRPTSTVDGKTTILKFEPLQKV     S (A)
         CTRQIILALPVPALMQVDWPPLRENRAQKAYGAVRTIPAS     L
         ||||||||||||||||||||||||||||||||||||||||
         CARQIILALPVPALMQVDWPPLRENRAQKAYGAVRTIPAS     S

KVFMTFDQPWWLQNDVTDFPAFVTKGDTTFSQMYDWKKSE     L
         |||||||||||||||||||||||||||||||||||||*** 
         KVFMTFDQPWWLQNDVTDFPAFVTKGDTTFSQMYDWKKPN     S

ASGDYILIASYADGNNTLFQRVLRDQGEPINGSEAGAHIV     L
         *|||||||||||||
         VSGDYILIASYADGSTQPWIH                        S

SEPLKNQILDHLADAFGVPRSDIQEPKTAVSKFWTDYPFG     L

CGWITWRAGYHFDDVMNTMRRPSLTDEVYVVGADYSWGLI     L

SSWVEGALETSYEVIDTYFKSERSHNVQPPSHMASHVG       L
```

Fig. 2(a)

```
GCC TAC CTT TTG AGG AAT AAA GGT CAG AAC
ATC GGG GTC TTC GAA TTC TGT GAC AGA GTG
GGT GGT CGG CTG TTC ACC TAT CAG TTG CCT
AAT ACC CCC GAC GTG CAG CTG GAA CTG GGG
GGG ATG CGG TAC ATC ACC GGC GCT CAT AAC
CTG CTC GAG GGA GTC GTT CGT CAG CTG GGA
CTG ACC CCA GTA GTG TTT ACA GAA GGC TTC
GGT AAG CTG GGC CGT ACA CGC TAT TAC CTG
AGG GGA CAG TCC CTG ACC TTC CAG GAA GTG
CTG ACA GGC GAC GTG CCA TAC AAC CTT ACC
GTC GCG GAG AAG CAG AAC CAG GAC AAT ATT
TTC GCC TTC TAT CTC AAG GAA CTA ACC CGT
TTC GAC GTA GGC GAC GGT TTC GTG ACC AGA
GAA CAA CTG CTG AAA CTG CGC GTC AGC GAT
GGG AGG CTC CTC TAC CAA CTG ACG TTC GAC
GAA GCC CTG GAC CTG GTA GCA TCG CCG GAA
GGT AAA GAA TTT GCC AGG GAC ATT CAC GTG
TTT ACG ACG GAG GTT TCA GAC GAC GCC AAC
GCG GTT TCG GTG TTC GAC GAC CAC TTA GGT
GAG GAC GGC GTA GGC GAG GAG ATC CAT ACC
GTG CAA GAA GGA ATG CAG AAA GTA CCG GAG
CAA CTG CTG CGT GCA TTT GGA AAC AGT TCC
GTC TTC GGC CAC AGG GTC TTC ACT AAC CTG
CAA CTG AAA GCA ATT CGA AGC AAA TCC GAC
AAG AGC CAC GTC CTG TAC TTT AGG ACC ACC
TCC ACG GTT GAC GGC AAA ACA ACA ATT CTC
AAA TTC GAG CCG CTG CAG AAG GTC TGC ACG
CGT CAG ATT ATC CTA GCT CTG CCT GTG TTC
GCC CTC ATG CAG GTC GAT TGG CCT CCC CTG
CGT GAG AAT CGG GCG CAG AAG GCG TAC GGC
GCG GTC AGG ACC ATT CCA GCG AGC AAG GTC
TTC ATG ACG TTC GAC CAA CCG TGG TGG CTT
CAG AAC GAT GTG ACA GAC TTC CCA GCG TTT
GTG ACC AAA GGA GAC ACC ACT TTC TCG CAA
ATG TAC GAC TGG AAA AAG TCC GAG GCT TCT
GGT GAC TAC ATC CTC ATC GCT TCG TAC GCC
GAC GGC AAC AAT ACC CTC TTC CAG AGG GTG
CTG CGC GAC CAA GGG GAG CCG ATC AAC GGC
AGT GAA GCC GGC GCC CAC ATC GTG TCC GAG
CCC CTT AAG AAC CAA ATT TTG GAC CAC CTC
GCG GAC GCG TTT GGC GTC CCC CGT TCG GAC
ATT CAG GAG CCC AAA ACG GCG GTC AGC AAG
TTT TGG ACT GAC TAC CCG TTT GGG TGT GGA
TGG ATT ACA TGG CGG CCG GGC TAC CAC TTC
GAC GAT GTG ATG AAC ACC ATG CGC AGA CCC
TCA CTC ACC GAC GAG GTC TAC GTT GTG GGT
GCG GAC TAC TCT TGG GGC CTT ATT TCT TCC
TGG GTG GAA GGC GCC CTG GAA ACC TCC TAC
GAG GTA ATC GAT ACA TAC TTC AAA AGC GAG
CGG TCA CAT AAT GTG CAA CCT CCA AGC CAC
ATG GCC TCC CAC GTG GGC
```

Fig. 2(b)

```
AYLLRNKGQNIGVFEFCDRVGGRLFTYQLPNTPDVQLELGGMRYITGAHNLLEGVVRQLG
         10        20        30        40        50        60

LTPVVFTEGFGKLGRTRYYLRGQSLTFQEVLTGDVPYNLTVAEKQNQDNIFAFYLKELTR
         70        80        90       100       110       120

FDVGDGFVTREQLLKLRVSDGRLLYQLTFDEALDLVASPEGKEFARDIHVFTTEVSDDAN
        130       140       150       160       170       180

AVSVFDDHLGEDGVGEEIHTVQEGMQKVPEQLLRAFGNSSVFGHRVFTNLQLKAIRSKSD
        190       200       210       220       230       240

KSHVLYFRTTSTVDGKTTILKFEPLQKVCTRQIILALPVFALMQVDWPPLRENRAQKAYG
        250       260       270       280       290       300

AVRTIPASKVFMTFDQPWWLQNDVTDFPAFVTKGDTTFSQMYDWKKSEASGDYILIASYA
        310       320       330       340       350       360

DGNNTLFQRVLRDQGEPINGSEAGAHIVSEPLKNQILDHLADAFGVPRSDIQEPKTAVSK
        370       380       390       400       410       420

FWTDYPFGCGWITWRAGYHFDDVMNTMRRPSLTDEVYVVGADYSWGLISSWVEGALETSY
        430       440       450       460       470       480

EVIDTYFKSERSHNVQPPSHMASHVG
        490       500
```

CYTOTOXIC CYPLASIN OF THE SEA HARE, APLYSIA PUNCTATA, CDNA CLONING AND EXPRESSION OF BIOREACTIVE RECOMBINANTS

CROSS-REFERENCE TO RELATED APPLICATIONS

This application is filed under the provisions of 35 U.S.C. §371 and claims the priority of International Patent Application No. PCT/EP02/14511 filed Dec. 18, 2002, which in turn claims priority of European Patent Application No. 02000388.5 filed on 7 Jan. 2002 and European Patent Application No. 02019914.7 filed on 4 Sep. 2002.

FIELD OF THE INVENTION

The present invention relates to a nucleic acid coding for a protein called "cyplasin" that shows a preferential toxicity to autonomously growing mammalian cells. Cell death induced by this protein differs from both apoptosis and necrosis. An intracellular cell death which occurs when recombinantly preparing cyplasin in cell cultures can be avoided by removal of the secretion signal in the cyplasin sequence. This modification makes it possible to express the cyplasin in a mammalian cell culture which is preferable with regard to the glycosylation pattern of the obtained protein. Thus, the present invention also relates to a method of recombinantly producing a protein in eukaryotic cells, preferably mammalian cells, which is cytotoxic for said cells when applied externally.

BACKGROUND OF THE INVENTION

Marine organisms represent an essentially unexploited reservoir for genes and metabolic products of potential biological and/or pharmacological interest [1, 2, 3]. So far, literature on natural products derived from marine organisms is dominated by low molecular weight compounds characterized by cytotoxicity. A number of such natural drugs are either clinically applied or under evaluation as potential anticancer drugs [1, 2, 3]. In contrast, reports on exploitable genes from marine organisms and their products are rare. The green fluorescent protein from the jellyfish *Aequorea victoria* may serve as an example for a gene of basic biological interest, which is widely used in biotechnology as reporter for studies on gene expression and protein localization in living cells [4].

Sea hares appear to represent another species producing high molecular weight gene products of interest. Originally, the toxicity of the mollusc *Aplysia* was found to be due to low molecular weight metabolic substances deriving from algal diet [5]. However, cytolytic, antimicrobial and antifungal activities could be detected in biochemical isolates of high molecular weight from the sea hares *Aplysia kurodai*, *Aplysia juliana* and *Dolabella auricularia*. Accordingly it was suggested that these organisms might produce water-soluble gene-expressed biopolymeres of pharmacological interest [5, 6]. Furthermore, these biochemical investigations suggest that sea hares produce a number of closely related glycoproteins of different sizes and with different biological activities. First attempts to characterize these proteins on the sequence level led to the molecular cloning of one *Aplysia kurodai*-derived cDNA which showed significant sequence identities with the cDNA encoding a protein produced by the giant African snail *Achatina fulica* [7]. However, a clear correlation of the protein encoded by the cloned *Aplysia kurodai* cDNA with any biological activity is missing. This is most likely due to the fact that the biologically active molecules are glycoproteins and that recombinant expression in *E. coli* results in biologically inactive proteins.

SUMMARY OF THE INVENTION

Thus, the technical problem underlying the present invention was to provide means for recombinantly producing cytotoxic proteins like cyplasin from *Aplysia* in a biologically active form.

The solution to said technical problem is achieved by providing the embodiments characterized in the claims.

The potential pharmacological value of *Aplysia*-derived proteins stimulated the approach of the present inventors to identify cytotoxic activities of the European sea hare *Aplysia punctata* on the sequence level. A bioassay-guided fractionation of the secreted mucus of albumen glands released a 56 kDa glycoprotein which showed cytotoxic effects on autonomously growing cells in nanomolar concentrations. Based on its cytotoxicity, its possible effects on neoplasia and its origin *Aplysia*, the protein was termed cyplasin. Cyplasin shows a preferential toxicity to autonomously growing transformed mammalian cells. Cell death induced by this protein differs from both, apoptosis and necrosis. The cytotoxic effects are irreversible and become apparent at nanomolar concentrations in a cell type-dependent manner. In contrast, injection of micromolar concentrations into mice is tolerated without apparent negative consequences. Microsequencing of the 56 kDa protein released a peptide sequence whose corresponding nucleotide sequence was used as probe to screen *Aplysia punctata* RNA-based cDNA and to select cDNA clones encoding polypeptides comprising the target peptide. Two closely related cDNAs were detected. The cDNA encoding a polypeptide 558 aa in length was considered to reflect a bona fide clone encoding the cytotoxic protein. Its protein-coding section was recloned in vectors suitable for expression in *E. coli*, in mammalian cells and in insect cells, respectively. The *E. coli*-expressed polypeptide was biologically inactive. Transfected mammalian cells expressed a cytotoxic factor and died thereof as if treated with the genuine cytotoxic protein. In contrast, transfected insect cells which proved to be much less sensitive when treated with the genuine protein expressed the cytotoxic factor and continued to proliferate allowing to establish stable insect cell lines expressing sufficient amounts of the cytotoxic factor for further characterization. Finally, it could be shown that a biologically active protein could be recombinantly produced in mammalian cells when using a DNA sequence encoding the protein without the secretory signal sequence.

The figure shows a 12% SDS polyacrylamide gel loaded with the most active fraction (lane cyplasin). The proteinaceous material migrates with an apparent molecular mass of 56 kDa. Lane M is loaded with marker proteins.

FIG. 2: (a) Amino acid sequences of precursor proteins derived from *A. punctata* cDNAs comprising the nucleotide sub-sequences coding for the (underscored) internal peptide SGDYILIASYAD (SEQ ID NO: 4)

The upper sequence (SEQ ID NO: 1; 558 aa residues) is derived from the nucleotide sequence of the cDNA encoding the polypeptide termed cyplasin-L, and the lower sequence (SEQ ID NO: 2; 421 aa residues) is derived from the nucleotide sequence of the cDNA encoding the polypeptide termed cyplasin-S. The nucleotide sequences are found in databases under the accession numbers AJ304802 (cyplasin-L cDNA) and AJ304801 (cyplasin-S cDNA). In addition to these clearly distinguishable transcripts other mRNAs may exist with additional differences. PCR with total cDNA as template and cyplasin-L specific primer pairs releases sequences slightly differing from the cloned cyplasin-L and cyplasin-S encoding cDNA sequences. Amino acid exchanges detected by the PCR procedure are indicated in brackets. Asn-linked glycosylation sites are found at aa positions N-151, N-271, N-401, N-416 and N-422. The putative cleavage point of the secretory signal sequence is between aa 52 (S) and aa 53 (A).

(b) Nucleotide sequence of the protein Cypl-Mut-(-Sig-.Seq) (SEQ ID NO: 5)

Figure 3:
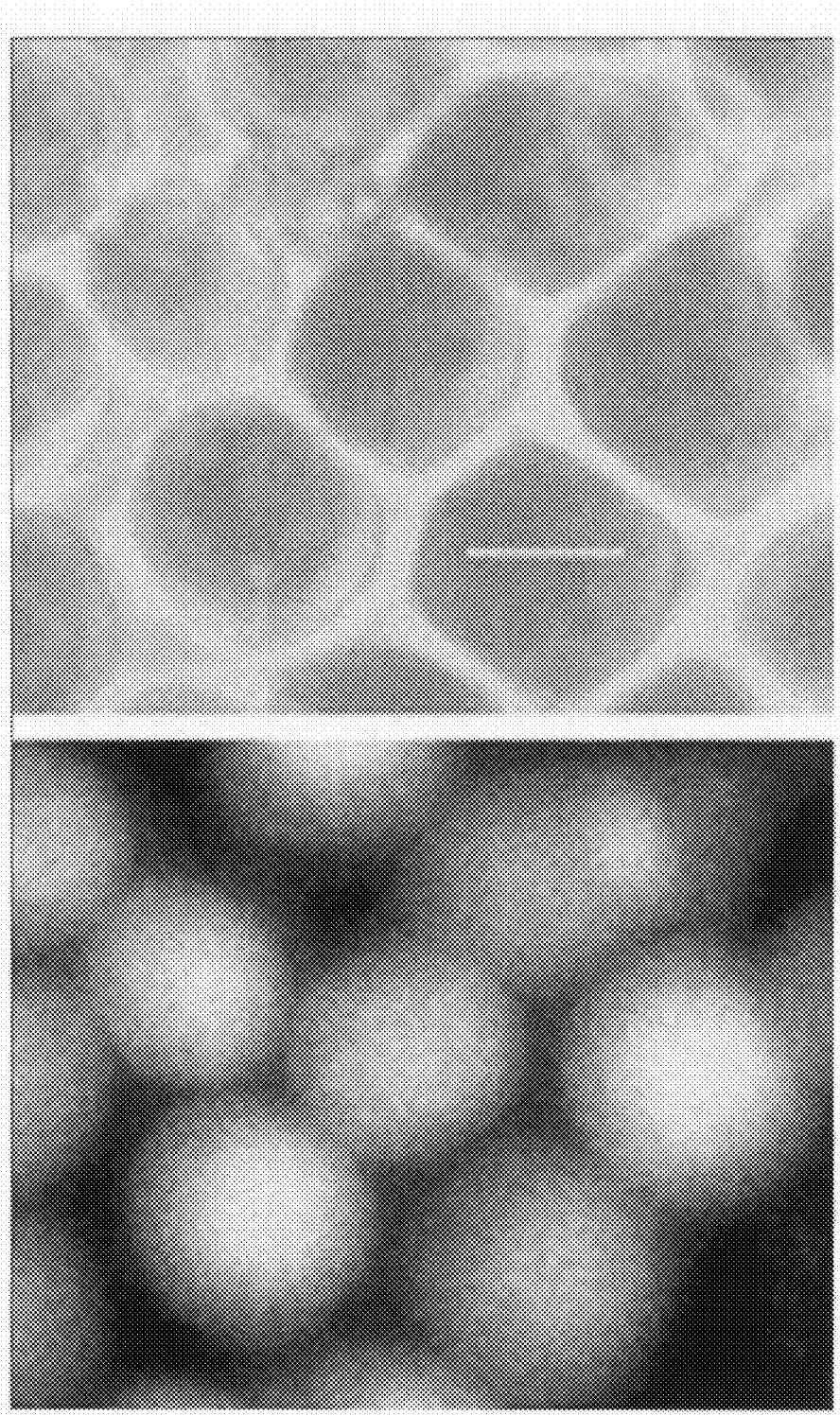

FIG. 3: Insect cells (Sf9) transfected with the pIZ vector-driven construct expressing cyplasin-L-EGFP The upper panel shows Sf9 cells in bright field and the lower panel shows the identical section in fluorescence mode (515 nm). Bar 10 µM.

Figure 4:
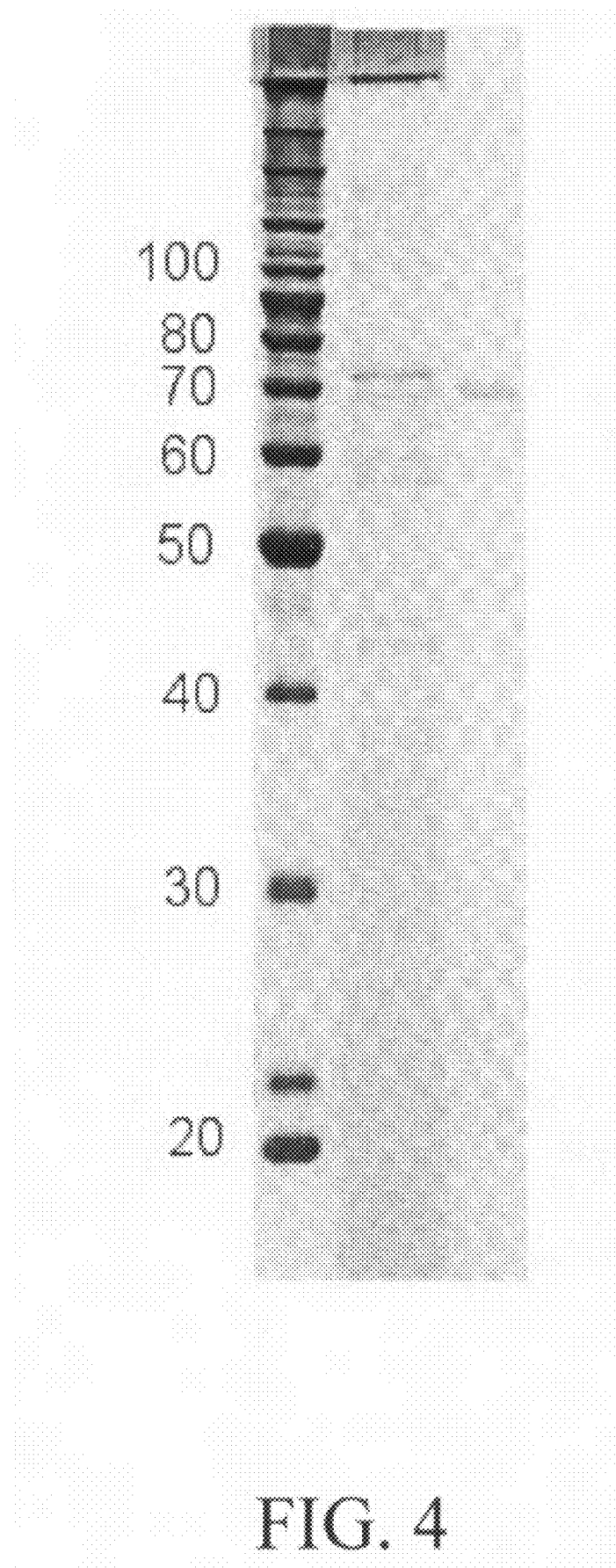

FIG. 4: Enrichment of the recombinant cyplasin-L-EGFP fusion protein in cytotoxic protein fractions released from SF9 cells Extracts containing the cytotoxic factor were prepared from SF9 cells expressing cyplasin-L-EGFP as described under materials and methods. Identical samples were separated on a 12% polyacrylamide gel. Polypeptides run on parallel gel sections together with a protein size marker were either visualized by a silver-staining procedure or blotted to a PVDF membrane. The membrane was probed with an anti-EGFP antibody and immuno-complexes formed were visualized by means of an alkaline phosphatase-coupled second antibody. The left lane of the gel in FIG. 4 shows the protein size marker. The middle lane of the gel in FIG. 4 shows the prominent polypeptides present in the extract, and the right lane of the gel in FIG. 4 shows the antigen detected by the EGFP-specific antibody. It should be noted that the anti-EGFP antibody detects a polypeptide in the order of 70 kDa which is significantly larger than EGFP (27 kDa). This result indicates the enrichment of the EGFP-tagged fusion protein in the cytotoxic fraction. The calculated molecular mass of the fusion protein between the cyplasin-L precursor protein (57.2 kDa) and EGFP is 84.2 kDa. The processed cyplasin-L with deleted signal sequence has a calculated molecular mass of 41.6 kDa resulting in a molecular mass of 68.6 kDa when fused to EGFP which is close to the size of the fusion protein detected on the blot. Accordingly, it has to be assumed that the cytotoxic extract contains the EGFP-tagged and processed cyplasin-L.

Figure 5:
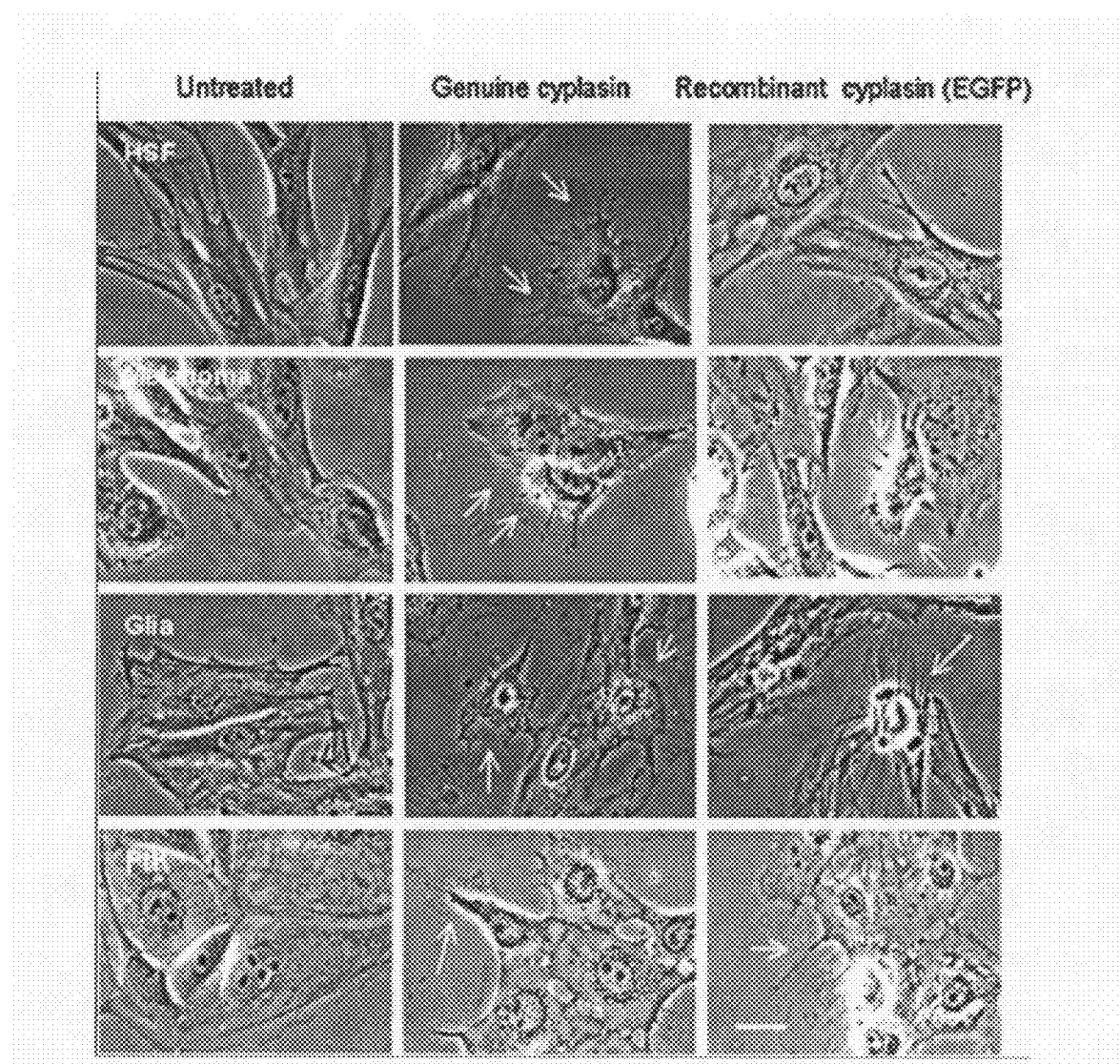

FIG. 5: Cytotoxic effects of genuine and recombinant cyplasin-L-EGFP

Four different cell lines were treated for five hours with genuine cyplasin and with standard extracts (Example 1) from SF9 cells stably expressing cyplasin-L-EGFP. Genuine cyplasin: Primary human skin fibroblasts (HSF), incubated with 50 nM cyplasin. At this concentration HSF cells show a slight but typical reaction that implies retraction of the cell membrane and partial detachment. Cell death is not observed at this concentration. The cells recover and continue to proliferate. Primary human melanoma cells derived from biopsies are more susceptible to the cytotoxic effect of cyplasin than HSF cells. After addition of cyplasin (2 nM) the cells show the typical cyplasin-induced membrane changes and finally die. Glia cells from a permanent cell line originating from the brain cortex of rat embryos are most sensitive when treated with cyplasin. Addition of 0.5 nM cyplasin is sufficient to induce cell death. Rat kangaroo PtK cells require 2 nM cyplasin to exhibit the morphology of dying cells. Recombinant cyplasin-L-EGFP: Standard extracts of recombinant cyplasin-L-EGFP (100 µl/500 µl medium) show, in parallel cultures, essentially identical and graded cytotoxic effects. Bar 10 µM.

Figure 6:
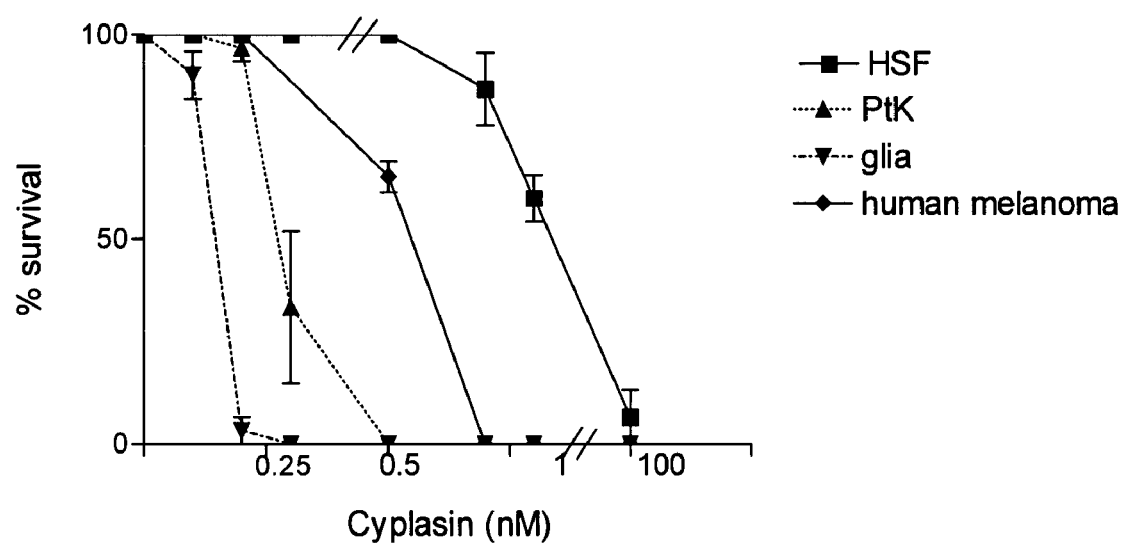

FIG. 6: Dose-response curve of cyplasin for various cell lines

Glia cells are the cells most sensitive to cyplasin. Less than 1 nM cyplasin suffices to kill the majority of them. Primary human melanoma cells and PtK cells show also high sensitivity to cyplasin, whereas HSFs are much more tolerant; only a dose as high as 100 nm cyplasin will kill these cells.

Figure 7:
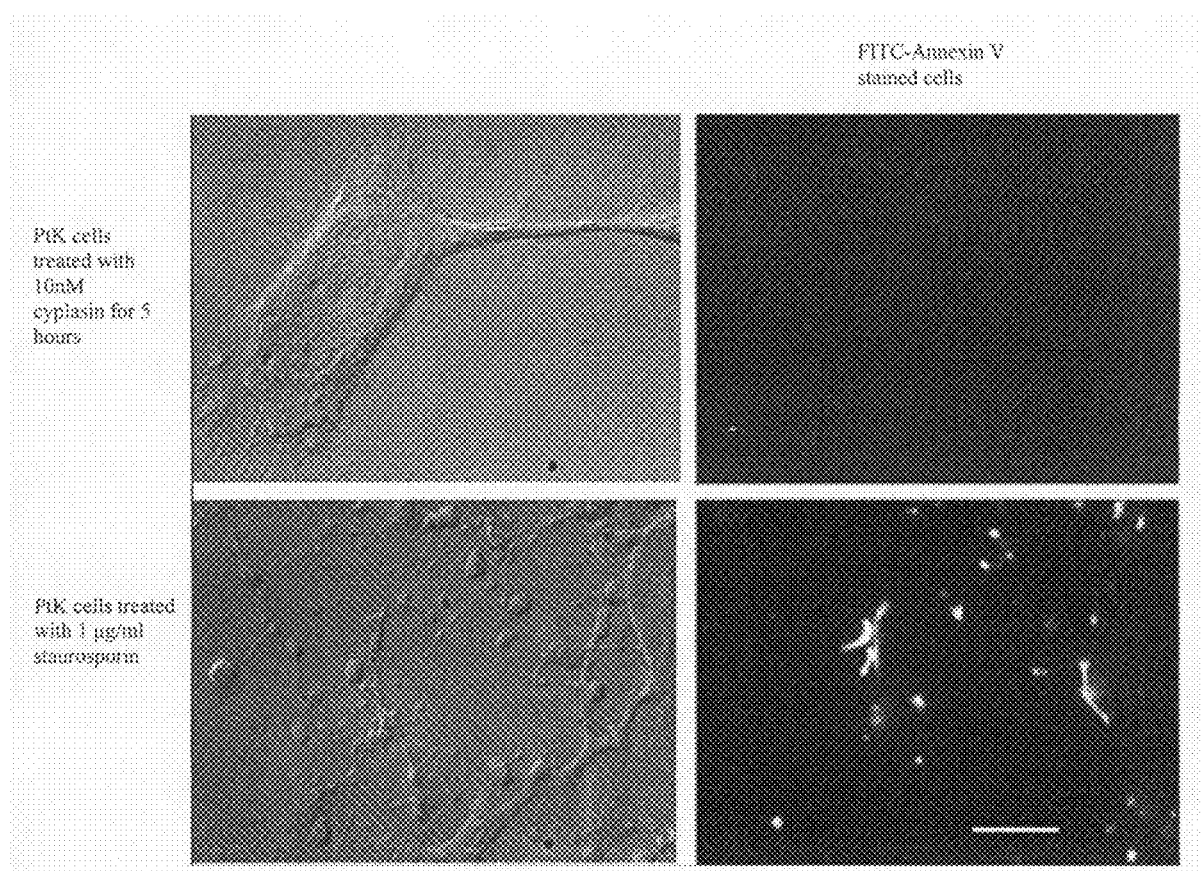

FIG. 7: Apoptotic cell death induced by staurosporine and cell-death induced by genuine cyplasin PtK cells were treated with 10 nM cyplasin for 5 hours (upper panel), or with 1 µg/ml staurosporin for three hours (lower panel). The cells were stained with a mixture of FITC-labeled annexin V and propidium iodide as described elsewhere in detail [8]. The FITC-Annexin V staining shows the characteristic translocation of phosphatidylserine from the inner to the outer side of the plasma membrane. No FITC-Annexin V staining is found in cyplasin-treated cells that show the characteristic cyplasin-induced morphological changes. Neither staurosporine nor cyplasin permeabilize the cells, which is revealed by missing propidium iodide staining of nuclei. Bar 10 µM.

Figure 8:
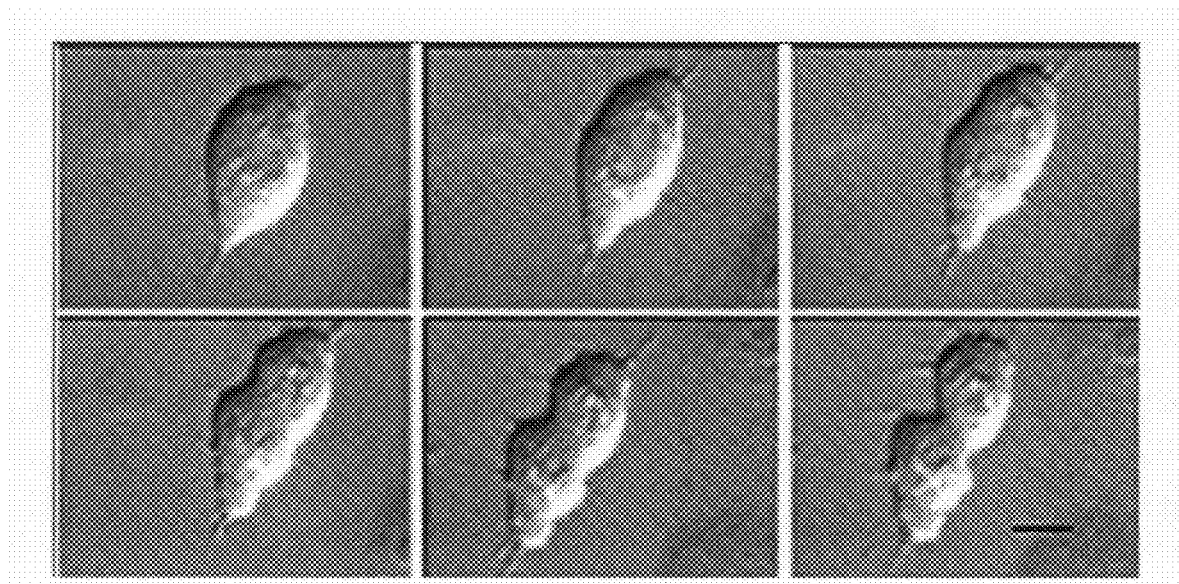

FIG. 8: Anaphase progress of a PtK cell present in a culture treated for one hour with 2 nM genuine cyplasin From upper left to lower right: No interference is observed with the process of anaphase, which is terminating in an apparently normal cytokinesis. After entering interphase this cell showed the typical cyplasin-induced changes in morphology. Bar 10 µm.

Figure 9:
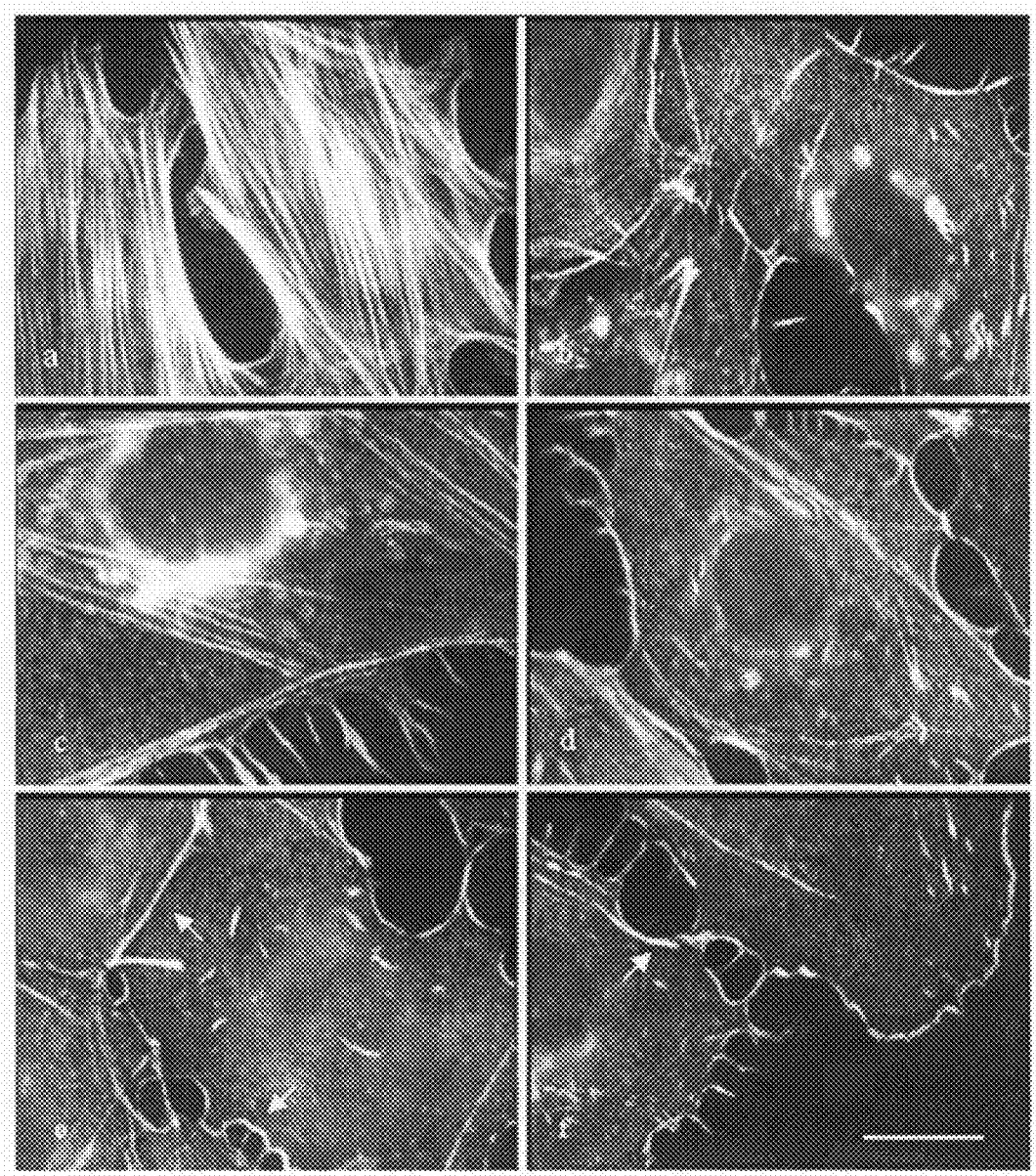

FIG. 9: Effect of cyplasin on the actin cytoskeleton of human primary melanoma cells Cyplasin (10 nM) causes a fast depolymerization of actin fibers, with the exception of the cortical area where 1-actin staining persists (arrows). (a) Intreated control; 8b) 30-minute cyplasin incubation; (c) 60-minute cyplasin incubation; (d) 90-minute cyplasin incubation; (e) 120-minute cyplasin incubation; (f) 150-minute cyplasin incubation. Bar 10 µm.

Figure 10:
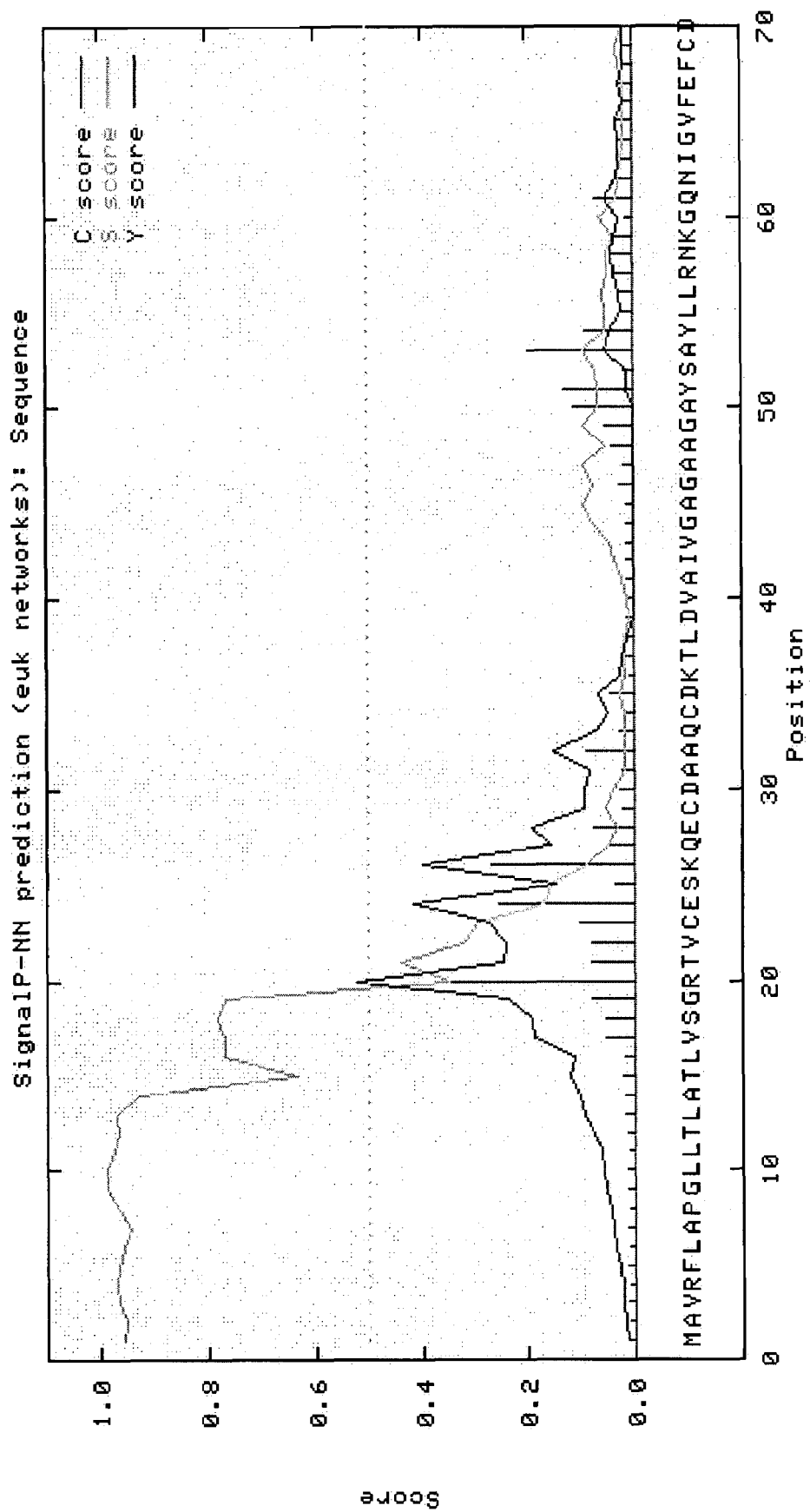

FIG. 10: Prediction of the signal peptide and its cleavage site in the N-terminal amino acid sequence of cyplasin The highest probability for cleavage was determined to be between aa positions 19 and 20 of SEQ ID NO: 1 or 2 or (with lower probability) between aa positions 52 and 53 of SEQ ID NO: 1 or 2.

FIG. 11: Amino acid sequence of the cyplasin with removed secretory leader sequence In human cells transfected with cDNA encoding this cyplasin variant of the protein (which is still cytotoxic) remains in the cytoplasm of the cells.

Figure 12:
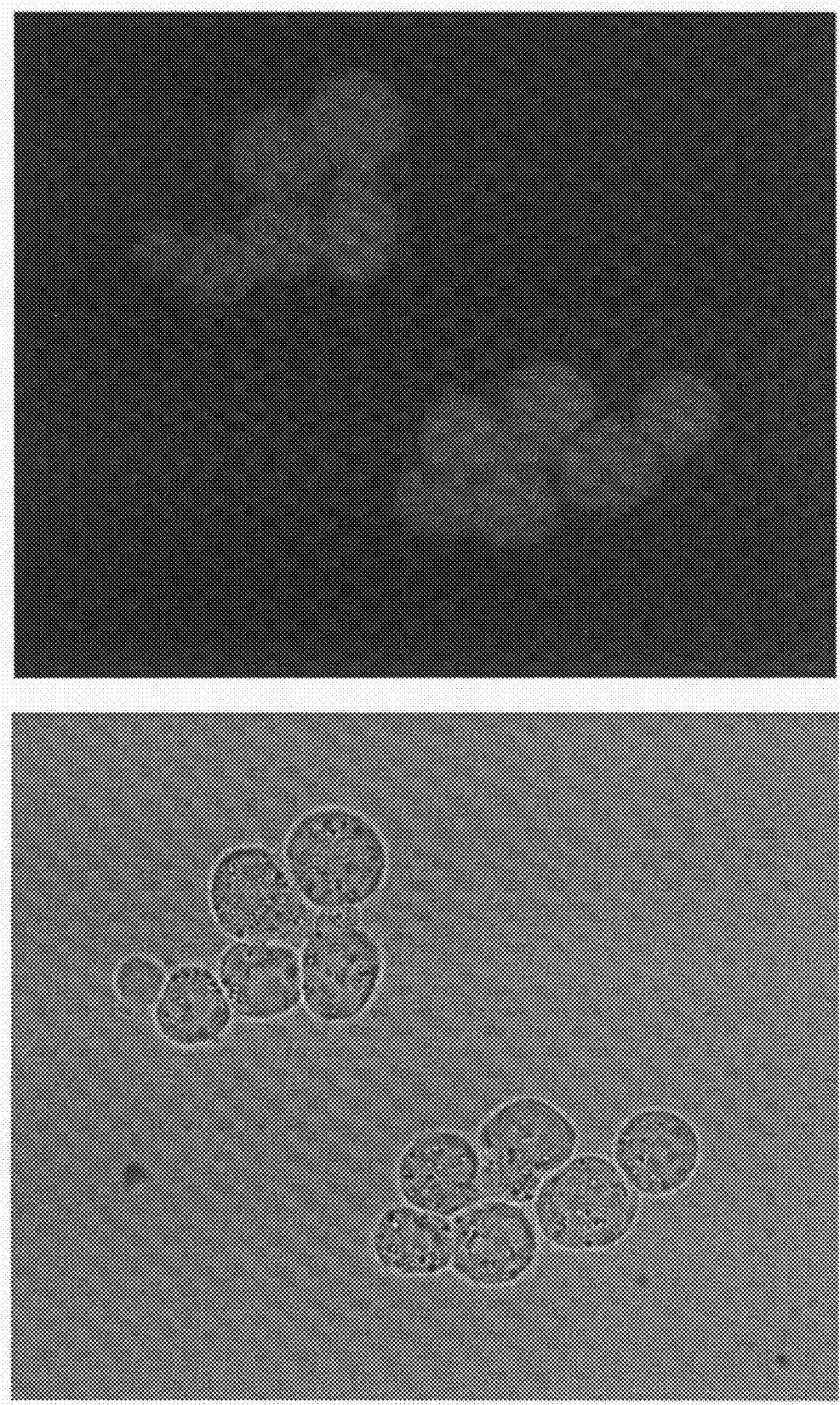

FIG. 12: Micrograph of HeLa cells transfected with the modified cyplasin cDNA Lower panel: bright field; upper panel: identical section in fluorescence mode. All cells contain EGFP and, as a consequence, cyplasin.

DETAILED DESCRIPTION OF THE INVENTION

Thus, the present invention relates to an isolated nucleic acid molecule encoding the protein cyplasin with a deleted or non-functional secretory signal sequence or a protein exhibiting biological properties thereof, being selected from the group consisting of
  (a) a nucleic acid molecule encoding a protein comprising the amino acid sequence from position 20 or 53 to position 558 of FIG. 2(a);
  (b) a nucleic acid molecule comprising the nucleotide sequence of FIG. 2(b)
  (c) a nucleic acid molecule the nucleic acid sequence of which deviates from the nucleic sequences specified in (a) or (b) due to the degeneration of the genetic code; and
  (d) a nucleic acid molecule, which represents a fragment, derivative or allelic variation of a nucleic acid sequence specified in (a), (b) or (c).

As used herein, a protein exhibiting biological properties of cyplasin is understood to be a protein having at least one of the biological activities of cyplasin, e.g. cytotoxic activity.

As used herein, the term "isolated nucleic acid molecule" includes nucleic acid molecules substantially free of other nucleic acids, proteins, lipids, carbohydrates or other materials with which it is naturally associated. For example, an isolated nucleic acid molecule could be part of a vector or a composition of matter, or could be contained within a cell, and still be "isolated" because that vector, composition of matter, or particular cell is not the original environment of the nucleic acid molecule.

The nucleic acid molecules of the invention can be both DNA and RNA molecules. Suitable DNA molecules are, for example, genomic or cDNA molecules. It is understood that all nucleic acid molecules encoding all or a portion of cyplasin are also included, as long as they encode a protein with biological activity. The nucleic acid molecules of the invention can be isolated from natural sources or can be synthesized according to known methods.

The nucleic acid molecules of the present invention also include molecules with sequences that are degenerate as a result of the genetic code.

In a further embodiment, the present invention provides nucleic acid molecules which comprise fragments, derivatives and allelic variants of the nucleic acid molecules described above encoding a protein of the invention. "Fragments" are understood to be parts of the nucleic acid molecules that are long enough to encode one of the described proteins. These fragments comprise nucleic acid molecules specifically hybridizing to transcripts of the nucleic acid molecules of the invention. These nucleic acid molecules can be used, for example, as probes or primers in a diagnostic assay and/or kit and, preferably, are oligonucleotides having a length of at least 15, preferably at least 50 nucleotides. The nucleic acid molecules and oligonucleotides of the invention can also be used, for example, as primers for a PCR reaction.

The term "derivative" in this context means that the sequences of these molecules differ from the sequences of the nucleic acid molecules described above at one or several positions but have a high level of identity to these sequences. Identity hereby means a sequence identity of at least 40%, in particular an identity of at least 60%, preferably of more than 80% or 85% and particularly preferred of more than 90%, 92%, 95% or 98%. These proteins encoded by the nucleic acid molecules have a sequence identity to the claimed amino acid sequence depicted in FIG. 2 of at least 60% or 70%, preferably of 80% or 85% and particularly preferred of more than 90%, 95%, 97% and 99%. The deviations to the above-described nucleic acid molecules may have been produced by deletion, substitution, insertion or recombination.

The nucleic acid molecules that are homologous to the above-described molecules and that represent derivatives of these molecules usually are variations of these molecules that represent modifications having the same biological function. They can be naturally occurring variations, for example sequences from other organisms, or mutations that can either occur naturally or that have been introduced by specific mutagenesis. Furthermore, the variations can be synthetically produced sequences. The allelic variants can be either naturally occurring variants or synthetically produced variants or variants produced by recombinant DNA processes.

Generally, by means of conventional molecular biological processes it is possible (see, e.g., Sambrook et al., 1989, Molecular Cloning, A Laboratory Manual, $2^{nd}$ edition Cold Spring Harbor Laboratory Press, Cold Spring Harbor, N.Y.) to introduce different mutations into the nucleic acid molecules of the invention.

For the manipulation in prokaryotic cells by means of genetic engineering the nucleic acid molecules of the invention or parts of these molecules can be introduced into plasmids allowing a mutagenesis or a modification of the sequence by recombination of DNA sequences. By means of conventional methods (cf. Sambrook et al., 1989, Molecular Cloning: A Laboratory Manual, $2^{nd}$ edition, Cold Spring Harbor Laboratory Press, NY, USA) bases can be exchanged and natural or synthetic sequences can be added. In order to link the DNA fragments with each other adapters or linkers can be added to the fragments. Furthermore, manipulations can be performed that provide suitable cleavage sites or that remove superfluous DNA or cleavage sites, preferably removal of the secretion signal. If insertions, deletions or substitutions are possible, in vitro mutagenesis, primer repair, restriction or ligation can be performed. As analysis method usually sequence analysis, restriction analysis and other biochemical or molecular biological methods are used.

The proteins encoded by the various variants of the nucleic acid molecules of the invention show certain common characteristics, such as enzyme activity, molecular weight, immunological reactivity or conformation or physical properties like the electrophoretical mobility, chromatographic behavior, sedimentation coefficients, solubility, spectroscopic properties, stability; pH optimum, temperature optimum.

The invention furthermore relates to vectors containing the nucleic acid molecules of the invention. Preferably, they are plasmids, cosmids, viruses, bacteriophages and other vectors usually used in the field of genetic engineering. Vectors suitable for use in the present invention include, but are not limited to the T7-based expression vector for expression in bacteria, the pMSXND expression vector for expression in mammalian cells and baculovirus-derived vectors for expression in insect cells. Preferably, the nucleic acid molecule of the invention is operatively linked to the regulatory elements in the recombinant vector of the invention that guarantee the transcription and synthesis of an RNA in prokaryotic and/or eukaryotic cells that can be translated. The nucleotide sequence to be transcribed can be operably linked to a promoter like a T7, metallothionein I or polyhedrin promoter.

In a further embodiment, the present invention relates to recombinant host cells transiently or stably containing the nucleic acid molecules or vectors of the invention. A host cell is understood to be an organism that is capable to take up in vitro recombinant DNA and, if the case may be, to synthesize the proteins encoded by the nucleic acid molecules of the invention. Preferably, these cells are prokaryotic or eukaryotic cells, for example mammalian cells, bacterial cells, insect cells or yeast cells. The host cells of the invention are preferably characterized by the fact that the introduced nucleic acid molecule of the invention either is heterologous with regard to the transformed cell, i.e. that it does not naturally occur in these cells, or is localized at a place in the genome different from that of the corresponding naturally occurring sequence.

A further embodiment of the invention relates to isolated proteins exhibiting biological properties of cyplasin, preferably cyplasin wherein the normally occurring secretion sequence has been removed or is non-functional, and being encoded by the nucleic acid molecules of the invention, as well as to methods for their production, whereby, e.g, a host cell of the invention is cultivated under conditions allowing the synthesis of the protein and the protein is subsequently isolated from the cultivated cells and/or the culture medium. Isolation and purification of the recombinantly produced proteins may be carried out by conventional means including preparative chromatography and affinity and immunological separations involving affinity chromatography with monoclonal or polyclonal antibodies. As used herein, the term "isolated protein" includes proteins substantially free of other proteins, nucleic acids, lipids, carbohydrates or other materials with which it is naturally associated. Such proteins however not only comprise recombinantly produced proteins but include isolated naturally occurring proteins, synthetically produced proteins, or proteins produced by a combination of these methods. Means for preparing such proteins are well understood in the art. The proteins of the invention are preferably in a substantially purified form.

In addition to cyplasin, there are a variety of proteins which are cytotoxic for tumor cells and, thus, might be of therapeutic value. For obtaining such proteins in sufficient quantity/quality they have to be recombinantly produced. Preferably, said proteins should be produced in mammalian cells, preferably in human cells, in order to ensure that the secondary modifications required for cytotoxic activity like glycosylation are present. However, in cases where the protein is secreted from the host cells and cytotoxic only if reacting with the outside of the cell membrane, its recombinant production can not be achieved since the secreted protein kills its host cells. It has been found by the present inventors that this problem can be overcome, i.e. that such a cytotoxic protein can be produced in mammalian cells if its export from the host cells is blocked after synthesis. This can be accomplished by expressing a gene encoding a protein without secretory leader sequence. Such a modified protein will remain in its host cell and, thus, is no longer cytotoxic for the cell. After lysis/homogenisation of the cells, the protein will be released and can be isolated and purified as a cytotoxic compound by established biochemical methods (see Example 11, below, relating to the recombinant production of cyplasin with removed secretory leader sequence in HeLa cells).

Thus, the present invention also relates to a general method of making a protein in eukaryotic host cells, preferably mammalian cells (e.g. HeLa cells), which is cytotoxic for said cells when externally applied, comprising:

(a) culturing a host cell transfected with a nucleic acid sequence encoding said protein with a deleted or non-functional secretory signal sequence under conditions such that said protein is expressed; and (b) recovering said protein from the cells.

Methods for the transfection of cells, recombinant production of proteins and recovery of the proteins from the cells have already been described above. The person skilled in the art can generate a nucleic acid sequence encoding a protein which is no longer secreted from the host cells by well known methods, e.g. by in vitro mutagenesis. Methods for determining the location/position of a secretory signal sequence are also well known and, e.g., described in [19-22].

Finally, the present invention also relates to a pharmaceutical composition comprising (i) a nucleic acid molecule, preferably a nucleic acid-molecule encoding the protein with or without the secretory leader sequence, or (ii) protein of the invention in combination with a pharmaceutically acceptable recipient, diluent or carrier as well as the use of said compounds for preparing a pharmaceutical composition for treating cancer.

Examples of suitable pharmaceutical carriers etc. are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Administration of the suitable compositions may be effected by different ways, e.g. by intravenous, intraperitoneal, subcutaneous, intramuscular, topical or intradermal administration. The route of administration, of course, depends on the nature of the tumor, its localisation and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind and stage of the tumor, general health and other drugs being administered concurrently.

The delivery of the nucleic acid molecules of the invention can be achieved by direct application or, preferably, by using a recombinant expression vector such as a chimeric virus containing these compounds or a colloidal dispersion system. Direct application to the target site can be performed, e.g., by ballistic delivery, as a colloidal dispersion system or by catheter to a site in artery. The colloidal dispersion systems which can be used for delivery of the above nucleic acid molecules include macromolecule complexes, nanocapsules, microspheres, magnetospheres, beads and lipid-based systems including oil-in-water emulsions (mixed), micelles, liposomes and lipoplexes, The preferred colloidal system is a liposome. The composition of the liposome is usually a combination of phospholipids and steroids, especially cholesterol. The skilled person is in a position to select such liposomes which are suitable for the delivery of the desired nucleic acid molecule organ-specific or cell-specific liposomes can be used in order to achieve delivery only to the desired tumor. The targeting of liposomes can be carried out by the person skilled in the art by applying commonly known methods. This targeting includes passive targeting (utilizing the natural tendency of the liposomes to distribute to cells of the RES in organs which contain sinusoidal capillaries) or active targeting (for example by coupling the liposome to a specific ligand, e.g., an antibody, a receptor, sugar, glycolipid, protein etc., by well known methods). In the present invention monoclonal antibodies are preferably used to target liposomes to specific tumors via specific cell-surface ligands.

Preferred recombinant vectors useful for gene therapy are viral vectors, e.g. adenovirus, herpes virus, vaccinia, or, more preferably, an RNA virus such as a Retrovirus. Even more preferably, the retroviral vector is a derivative of a murine or avian retrovirus. Examples of such retroviral vectors which can be used in the present invention are: Moloney murine leukemia virus (MoMuLV), Harvey murine sarcoma virus (HaMuSV), murine mammary tumor virus (MuMTV) and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance can be provided, e.g., by using helper cell lines that contain plasmids encoding all of the structural genes of the retrovirus under the control of regulatory sequences within the LTR. Suitable helper cell lines are well known to those skilled in the art. Said vectors can additionally contain a gene encoding a selectable marker so that the transduced cells can be identified. Moreover, the retroviral vectors can be modified in such a way that they become target specific. This can be achieved, e.g., by inserting a polynucleotide encoding a sugar, a glycolipid, or a protein, preferably an antibody. Those skilled in the art know additional methods for generating target specific vectors. Further suitable vectors and methods for in vitro- or in vivo-gene therapy are described in the literature and are known to the persons skilled in the art; see, e.g., WO 94/29469 or WO 97/00957.

In order to achieve expression only in the target organ, e.g., a particular tumor to be treated, the nucleic acid molecules of the present invention can be linked to a tissue specific promoter and used for gene therapy. Such promoters are well known to those skilled in the art (see e.g. Zimmermann et al., (1994) Neuron 12, 11-24; Vidal et al.; (1990) EMBO J. 9, 833-840; Mayford et al., (1995), Cell 81, 891-904; Pinkert et al., (1987) Genes & Dev. 1, 268-76).

The following Examples illustrate the invention.

In summary, the results of the Examples support previous suggestions pointing to cytotoxic substances of high molecular weight that are produced and secreted by *Aplysia* species [5, 6]. Protein fractions from the secreted mucus of *A. punctata* show cytotoxic and finally killing activity when added to cells that grow independently of proliferation-controlling activities, e.g. in culture. One of these factors has been characterized on the peptide sequence level and it has been termed cyplasin. Interestingly, cyplasin shows a graded cytotoxicity on cells in culture. It is highly cytotoxic to established cell lines, as shown for the glia cell line and PtK cells, as well as to many primary tumor cells, such as the human melanoma tested. Human skin fibroblasts show a significantly higher tolerance. Since other tumor cells tested are also highly sensitive (not shown) it appears that cyplasin is especially cytotoxic to established cell lines and to primary tumor cells. The different response of primary human fibroblasts is probably due to the fact that these cells cannot be considered as tumor cells although growing autonomously [17]. Accordingly, cyplasin might be useful for the specific elimination of non-desired cells in an organism, such as tumor cells.

Such a view is supported by preliminary in vivo experiments. In no case a toxic effect of the injected cyplasin was found when injected in normal mice, even when high concentrations of cyplasin were used.

The natural source for cyplasin is limited; hence, its recombinant production appears to be a prerequisite for its potential application as an anti-cancer drug. In a first step we searched for a cDNA, which could be considered to encode the protein with an apparent molecular mass of 56 kDa, which had been isolated by the bioassay-guided fractionation procedure. Using a subsequence of this protein as probe and conventional PCR and cDNA cloning techniques we found that more than one *A. punctata* transcript comprises the subsequence used as specific probe. Two cDNAs encoding polypeptides with diverging carboxy termini could be identified on the sequence level. Moreover, individual cDNA clones showed slightly diverging nucleotide sequences when PCR products were cloned which were prepared on the basis of complete *A. punctata* cDNA library template and primer pairs fitting the coding regions of the cDNAs identified in the first step. Actually, all individual clones investigated so far showed slightly different nucleotide sequences with the consequence of one or more amino acid exchanges in the corresponding polypeptide. It is highly unlikely that all these transcripts originate from different genes in *A. punctata*. Posttranslational processes like alternative splicing, differential polyadenylation and RNA editing could result in transcripts encoding the different polypeptides.

At this stage it is unknown whether the different polypeptides identified at the transcript level exhibit all identical functions. In this situation it appeared worthwhile to select only one cDNA species (encoding the protein termed cyplasin-L) and to investigate whether this sequence could encode a cytotoxic protein. The recombinant polypeptide produced in *E. coli* was found to be biologically inactive. However, eukaryotic cells transfected with constructs expressing this selected cDNA or this cDNA in fusion with the EGFP-encoding nucleotide sequence produced a cytotoxic factor that was not present in non-transfected cells nor in cyplasin-S transfected cells. Insect cells (Sf9) transfected with pIZ-driven expression constructs became especially useful. In this case stably transfected cell lines could be established which permitted the preparation of biologically active EGFP-tagged cyplasin-L in quantities sufficient to compare the biological activity-of the recombinant protein with the material that can be biochemically isolated from the secreted mucus of *A. punctata*. The very similar morphological effects achieved by the biochemical isolate and by the recombinantly expressed protein suggested that the selected cDNA is a valid clone and that it encodes a protein presenting the cytotoxic principle of the genuine cyplasin of *A. punctata*. Finally, it could be shown that biologically active cyplasin could be recombinantly produced in HeLa cells when using a DNA sequence encoding the protein without the secretory signal sequence. With the availability of bioactive recombinant cyplasin, it is now possible to evaluate its potential anti-tumor therapeutic value.

EXAMPLE 1

Materials and Methods (A) Biochemical Isolation of Cyplasin

Figure 1:
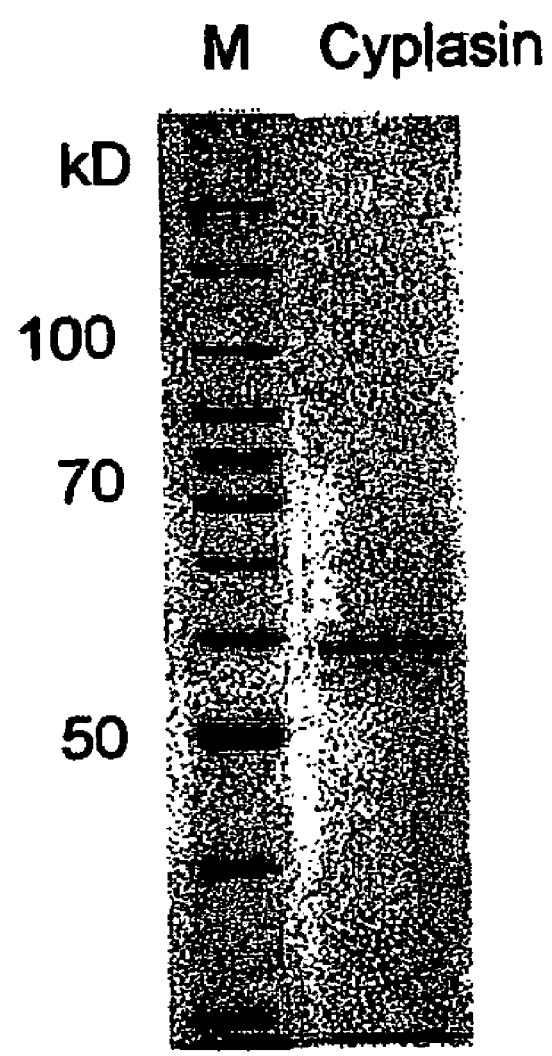
FIG. 1: SDS-polyacrylamide gel electrophoresis of cyplasin isolated by a bioassay-guided fractionation of the secreted mucus of *A. punctata*

Mucus of albumen glands of the sea hare *A. punctata* can be obtained from animals during the spawning season when they come to the shore (around April on Ile d'Yeu). By gently squeezing the animal, the mucus (approximately 2.5 ml) is excreted as purple fluid forming a gel when exposed to air. It is immediately diluted (1:1, vol/vol) with phosphate-buffered saline (PBS, 150 mM NaCl, 10 mM NaH$_2$PO$_4$, pH 7.2) and placed at 4° C. After 2-3 hours the mixture becomes completely soluble. This step is followed by centrifugation at 10.000×g, 15 min, 4° C., to remove debris. The supernatant can be frozen and kept at −80° C. without loss of activity. For further purification the mucus is dialysed against 1000 volumes of 50 mM MOPS, 1 mM dithioerythritol, 0.5 mM EDTA, 5 mM KCl, pH 7.2 for 24 hours at 4° C. Protein fractions containing the cytotoxic activity were isolated by fractionated precipitation with ammonium sulphate. Cytotoxic activity was detected in precipitates collected between 33%/50% (pellet 1) and 50%/66% (pellet 2) saturation, respectively. Most of the cytotoxic activity was usually found in pellet 1. For cytotoxicity tests pellets were dissolved in 300 µl PBS, dialysed against the buffer described above. The most active fractions comprised protein(s) migrating as an essentially single band on a SDS-PAGE gel (FIG. 1).

(B) Identification of the SGDYILIASYAD Peptide in the Fraction of Cytotoxic Protein(s)

Material used for the microsequencing procedure was further purified by gel filtration (G-200-column, Sigma-Aldrich, Taufkirchen, Germany) in a buffer comprising 50 mM MOPS, 1 mM dithioerythritol, 0.5 mM EDTA, 5 mM KCl, at pH 7.2. The dialyzed and lyophilized efflux was submitted to SDS-PAGE and blotted to a PVDF membrane (ProtoBlot, Applied Biosystems). Sections containing the region of interest were analysed by microsequencing procedures performed by WITA GmbH (Berlin, Germany).

(C) Cytotoxicity Test

Aliquots from each pellet, dissolved in 300 µl PBS, were tested for their toxic effect on autonomously growing cells. The term 'autonomously growing cells' is used for all cells capable of proliferating in vitro, in contrast to cells proliferating within an organism. Routine tests were performed using the rat kangaroo cell line PtK$_2$ and the human cell line HeLa. Cells were seeded in 24-well plates containing 500 µl medium per well, using cell densities resulting in about 50% confluency after 24 hours. At this time undiluted aliquots of the redissolved pellet(s) (5 µl) were added and cell cultures in parallel wells were supplemented with aliquots (5 µl) of serial dilutions.

(D) Characterization of Cell Death Induced by Genuine Cyplasin

Morphological alterations of cells undergoing cyplasin-induced death were recorded by light microscopy. In addition permeability changes of the plasma membranes were investigated by incubating the cyplasin-treated cells with the non-membrane permeant compound H33257 (SIGMA-ALDRICH, Taufkirchen, Germany), 0.5 µg/ml, or propidium iodide (Boehringer Ingelheim, Germany), 1 µg/ml. Staining of nuclei was considered as indication for pathological permeability changes associated with necrosis or the final stages of apoptosis. To differentiate the apoptotic form of death, cyplasin-treated cells were incubated in 5 µg/ml of FITC-labeled Annexin V (Boehringer Ingelheim, Germany) for 20 min in Ca$^{2+}$-containing buffer and the presence of a potential phosphatidyl serine-annexin complex was evaluated by fluorescence microscopy using appropriate filters (8). For control, apoptosis was induced in cells by incubation with 0.2 µg/ml staurosporine for three hours. This treatment induced a clear translocation of phosphatidylserine to the outer face of the plasma membrane, thus becoming accessible to the FITC-Annexin [9]; the concentration of staurosporine, however, was sufficiently low to prevent the parallel staining of cell nuclei with propidium iodide.

(E) A. punctata cDNA

Total RNA was isolated from albumen glands of the sea hare A. punctata by means of the Qiagen RNA isolation kit. The Clontech SMART II PCR cDNA synthesis kit (K1052-1) was used to convert 100 ng amounts of total RNA into cDNA. First strand synthesis was primed with the modified oligo-dT included in the kit and primer extension was performed with the recommended RNase H$^-$ point mutant reverse transcriptase (Superscript II, Gibco BRL). The SMART II oligo inducing the template switch at 5' ends was included in the first-strand reaction. These reactions and PCR amplifications of first-strand cDNA by means of the modified oligo (dT) and SMART II primers were performed according to the instructions of the producer of the kit.

(F) Molecular Cloning of cDNAs Encoding Proteins Comprising the Peptide SGDYILIASYAD (SEQ ID NO: 4)

Amplified cDNA was used as a template and PCR reactions were primed with combinations of specific primers corresponding to the search sequence and with non-specific primers, e.g. modified oligo-dT and Smart II, respectively. Amplification products were recloned in a pBluescript-derived T-overhang vector and sequenced. The validity of these sequences was verified by PCR reactions primed with oligo deoxynucleotides corresponding to sequences upstream and downstream of the specific SGDYILIASYAD-encoding primer. These probe-independent products contained the nucleotide sequence encoding the peptide SGDYILIASYAD (SEQ ID NO: 4). Sequences found upstream of SGDYILIASYAD-encoding sequence were unique, except for several base exchanges discussed in the text. In contrast, two 3' end sequences could be detected differing in length (L and S).

(G) Fusion and Expression Constructs

The protein-coding sections were PCR amplified with primers placing suitable restriction sites to the 5' and 3' ends of the amplification products. Following digestion with the corresponding restrictases the products were either directly cloned into the expression vectors pcDNA3 (Invitrogen, for expression in mammalian cells), pQE30 (Qiagen, for expression in E. coli), pIZ/V5-His (Invitrogen, for expression in insect cells) or fused with the EGFP-encoding cDNA (Clontech) prepared in the XhoI/NotI sites of the pBluescript vector. Excision of the EGFP-tagged fragments and recloning in appropriate sites of the pcDNA3 vector or the pIZ/V5-His vector resulted in the corresponding cyplasin-EGFP expression constructs suitable for expression of fluorescently labeled fusion proteins in mammalian and insect cells, respectively.

(H) Transfections and Recombinant Protein Expression

E. coli M15 cells were transformed with the pQE30 plasmids containing the cyplasin-L and cyplasin-S-encoding inserts in frame with the His-tag of the vector. The expressed His-tagged proteins were isolated by means of Ni-NTA agarose according to the protocol supplied by Qiagen. HeLa cells were transfected with the pcDNA3 plasmids containing either EGFP-tagged or non-tagged cyplasin-L and cyplasin-S-encoding inserts by means of the Effectene transfection kit (Qiagen). Cells transfected with constructs containing the insert encoding cyplasin-L or cyplasin-L-EGFP could not survive longer periods. However, supernatants of such cultures contained the cytotoxic factor described in the text. SF9 cells were transfected with the pIZ/V5-His plasmids containing either EGFP-tagged or non-tagged cyplasin-L encoding inserts using in addition the Effectene transfection kit (Qiagen). In contrast to mammalian cells transfected insect cells survived. Expression was followed either by fluorescence microscopy of living cells or by testing of cytosolic extracts for the presence of a cytotoxic factor.

(I) Stably-transfected SF9 Cells for Large Scale Production of Cyplasin-L-EGFP

SF9 cells transfected with the plasmid pIZ/V5-His-cyplasin-L-EGFP were grown for three months as semi-attached cells at 26° C. in TNM-FH insect medium (Applichem, Darmstadt, Germany) supplemented with 10% fetal calf serum, 5 mM Glutamax (LIFE Technologies, Karlsruhe, Germany) and 100 µg/ml zeocin (Invitrogen, Groningen, The Netherlands). The cell cultures were diluted 1:3 at four-day intervals. The original transfection efficiency was approximately 10%, after a three-months' period 5% of the cells remained fluorescent. The latter fraction was considered to be stably transfected. Cells of this fraction were separated by means of a fluorescence-activated cell sorter (Beckton-Dickinson). Following a second sorting performed after four weeks the resulting culture could be grown in spinner cultures up to several liters and more than 90% of these cells expressed cyplasin-L-EGFP fusion protein.

(J) Recovery of the Cytotoxic Factor from SF9 Cells Stably Expressing Cyplasin-L-EGFP The EGFP-tagged cyplasin-L is not secreted into the medium of SF9. Routinely, $1$-$2\times10^8$ stably transfected Sf9 cells were washed by suspension and centrifugation (1000× g, 3 min), once in PBS, and once in 50 mM MES, 1 mM EDTA, 5 mM KCl, 0.1% Mercaptoethanol, pH 6.0. They were homogenized in 5 ml of the latter buffer. Homogenization and all subsequent steps were performed at 4° C. A protease inhibitor cocktail (Roche Diagnostics, Mannheim, Germany) was present throughout the purification procedure. The homogenate was centrifuged (100,000×g, 60 min), and the supernatant was applied to a DEAE-Cellulose column (DE52, Sigma Aldrich, Taufkirchen, Germany) that had been equilibrated with the buffer described above. The column was washed extensively with the buffer used for equilibration followed by application of a NaCl-gradient (0-200 mM). Eluted fractions were tested for the presence of the cytotoxic factor by addition of 100 µl of each fraction to indicator cells (PtK) growing in 500 µl culture medium. If present, cytotoxic effects were observed after about five hours. Factor-containing fractions were eluted between 60 and 80 mM NaCl. Fractions with these characteristics were considered as 'standard' extracts, and used for other biological tests, e.g. those described in FIG. 5.

(K) Identification of Cyplasin-L-EGFP in Cytotoxic Extracts Isolated from Stably Transfected SF9 Cells Protein fractions isolated as described above and exhibiting cytotoxic activity were concentrated and separated by 12.5% SDS-PAGE. Two identical samples (including a protein standard) were separated on the same gel. One section of the gel was stained using a silver-staining procedure; the other section was electroblotted (semi-dry blotting apparatus, Biometra, Gottingen, Germany) to a PVDF transfer membrane (Westran, Schleicher & Schuell, Dassel, Germany). Buffer composition was 3.03 g boric acid, 200 ml methanol, 800 ml $H_2O$, pH 9.0. Following blocking with BLOTTO [10] the membrane was incubated for 3 hours (26° C.) with anti-GFP antibody (ABCAM, Cambridge, U.K.) diluted 1:2000 in PBS, pH 7.2, containing 0.1% BSA. After prolonged rinsing in PBS immunodetection was performed by means of an alkaline phosphatase-coupled goat-anti-rabbit antibody (Dianova, Hamburg, Germany) which was applied for three hours at 26° C., diluted 1:12000 PBS, pH 7.2, containing 0.1% BSA. The blot was rinsed in PBS and placed into the staining solution consisting of 100 mM TRIS, 5 MM $MgCl_2$, 0.3 mg/ml nitro blue tetrazolium, 0.15 mg/ml 5-bromo-4-chloro-3-indolylphospate, pH 9.5.

(L) Animal Experiments

DBA2 mice were injected with 300 µl (10 µM) genuine cyplasin, either in the tail vein (group 1) or subcutaneously (group 2). Cyplasin had been dialysed before against a large volume of PBS for 24 h at 4° C. and tested for positive cytotoxicity immediately before injection by incubating PtK cells with 10 nM cyplasin. Recombinant cyplasin was also dialysed against PBS, tested for positive cytotoxicity before injection, and 300 µl were injected into the tail vein. Mice were maintained under standard conditions and observed for four weeks.

(M) Stably-transfected HeLa Cells for Large Scale Production of Cyplasin-L-EGFP without Secretory Signal Sequence Following digestion with the corresponding restrictases the cyplasin L-(-Sig.Seq)-encoding cDNA was fused with the EGFP-encoding cDNA (Clontech, Heidelberg, Germany) prepared in the XhoI/NotI sites of the pBluescript vector. Excision of the EGFP-tagged fragments and recloning in the appropriate sites of the pcDNA3 vector (Invitrogen) resulted in the corresponding Cyplasin-L(-Sig.Seq.)-EGFP expression of the fluorescently labelled fusion proteins in mammalian cells. Selection of successfully transfected cells was achieved using G-418-sulfate resistance.

(N) Other Methods

Database searches and sequence analyses were performed by means of the HUSAR program package (DKFZ) that is a collection of sequence analysis tools based on the GCG program package developed by GCG Inc. (Madison, Wis., USA). For the identification of the secretory signal sequence we applied the McGeoch scan program [11]. DNA sequencing was performed by A. Hunziker (German Cancer Research Center) by means of an automatic DNA-sequencer, model 373A (Applied Biosystems).

EXAMPLE 2

Molecular Cloning of Cyplasin-encoding cDNAs cDNA prepared from RNA of the albumen gland of *A. punctata* comprises more than one transcript encoding the peptide SGDYILIASYAD (SEQ ID NO: 4). Two cDNAs were cloned encoding proteins which diverge significantly in their carboxy-terminal sections but which comprise the target sequence (FIG. 2). One of these cDNAs encodes a protein of 558 aa residues with a molecular mass of 62.4 kDa (termed cyplasin-L: SEQ ID NO: 1) while another cDNA reflects a transcript encoding a shorter protein (421 aa residues, molecular mass 46.9 kDa, termed cyplasin-S; SEQ ID NO: 2). Moreover, PCR on total cDNA with cyplasin-L specific primer pairs results in DNA fragments whose sequences diverge from those encoding cyplasin-L and cyplasin-S, respectively. Accordingly, mRNAs appear to exist which are neither identical with cyplasin-L nor with cyplasin-S. These sequence micro heterogeneities suggest that *A. punctata* produces an unknown number of very similar but not 100% identical proteins that comprise the target sequence. On the basis of the available data it cannot be decided whether these different mRNAs and proteins derive from one single gene, e.g. by alternative splicing in combination with RNA editing, or whether there exists a cluster of very similar but not 100% identical genes.

EXAMPLE 3

Sequence Characteristics of the Proteins Cyplasin-L and Cyplasin-S Encoded by the Cloned cDNAs Biochemical data suggest (not shown) that the naturally occurring cyplasin is a glycoprotein. The cyplasin-L cDNA-derived amino acid sequence comprises five Asn-linked (N-X-S or N-X-T) glycosylation sites at positions N-151, N-271, N-401, N-416 and N-422 that is in agreement with the biochemical data. The glycosylation sites 1-4 are unchanged in the polypeptide derived from the cyplasin-S cDNA while the position N-422 is missing in the shorter sequence.

The N-termini start with a hydrophobic secretory signal sequence of high probability and a predicted cleavage site between aa residues 52 (Ser) and 53 (Ala). Accordingly, the molecular masses of the mature and expectedly functional proteins amount to 57.2 kDa and 41.6 kDa, respectively. The calculated isoelectric points of these mature proteins are 5.54 (charge −13) for cyplasin-L and 6.20 (charge −5) for cyplasin-S.

Database searches with the nucleotide sequence released similarities with two other *Aplysia* sequences, namely *A. kurodai* albumen gland mRNA for aplysianin-A precursor ([12], 70.9% identities, D83255), and *A. fulica Ferussac* mRNA for achacin ([7], 52.2% identities, X64584). Database searches with cyplasin sub-sequences released the amino acid sequences of the *Aplysia* species mentioned above and a number of protein sequences with longer strings of local identities or homologies. The latter sequences all belong to the class of monoamine oxidases. Table 1 shows alignments of one prominent cyplasin peptide string with subsequences of eukaryotic and prokaryotic monoamine oxidases. It is of interest to note that database searches with this and other cyplasin-typical strings released no significant hits with proteins from other classes.

TABLE 1

Database searches with the pCyplasin-derived amino acid sequence resulted in a number of hits with sequences reflecting monoamine oxidases

| Sequence | | Accession no | Organism |
|---|---|---|---|
| 62 NIGVFEFCDRVGGRLFT 78 | | Cyplasin | A. punctata |
| + V E | DRVGGR FT | I51346 | Rainbow trout |
| + V E | +RVGGR+ T | OXLA_CROAD | Crotalus |
| N+ V E | +RVGGR +T | AOFA_BOVIN | Bovin |
| ++ V E | D VGGR +T | AOFB_RAT | Rat |
| ++ V E | DRVGGR +T | AOFA_HUMAN | Human |
| N+ V E | DRVGGR +T | AOFB_HUMAN | Human |
| ++ FE | +RVGGR+F+ | T08202 | Prokaryotic |
| +FE | DR+GGR+++ | T22714 | Prokaryotic |
| + VFE | DRVGGR T | AOFH_MYCTU | Prokaryotic |

TABLE 1-continued

Database searches with the pCyplasin-derived amino acid sequence resulted in a number of hits with sequences reflecting monoamine oxidases

| Sequence | | Accession no | Organism |
|---|---|---|---|
| ++ +FE | + VGGR T | TR2M_AGRVI | Prokaryotic |
| ++ V+E | DR+GG+L++ | TR2M_AGRRA | Prokaryotic |
| ++ ++E | DRVGG+L++ | A20966 | Prokaryotic |
| + + E | R GGR+ T | E69899 | Prokaryotic |
| ++ ++E | DRVGG+L++ | TR2M_AGRT3 | Prokaryotic |
| + V E | DRVGGR ++ | PUO_MICRU | Prokaryotic |

EXAMPLE 4

Expression of Biologically Inactive Recombinants in *E. coli*

Recombinant expression of cyplasin-encoding cDNA sequences in the pQE/*E. coli* M15 system results in polypeptides which are completely insoluble in buffers containing no detergents, and suspensions of such recombinantly expressed polypeptides could not exert any cytotoxic effect when incubated together with cultured cells (not shown). This missing cytotoxic activity is suggestively due to incorrect folding and/or the absence of posttranslational modifications of the polypeptides expressed in the *E. coli* system.

EXAMPLE 5

Generation of Bioactive Recombinants in Mammalian Cells

In contrast, mammalian cells, e.g. HeLa S3 suspension cells, produce a cytotoxic factor when transfected with CMV vector-driven expression constructs specifying either cyplasin-L or EGFP-tagged cyplasin-L. This factor is not detectable in cultures of non-transfected cells nor in cultures transfected with constructs expressing the cyplasin-S version. The production of the cytotoxic factor is obvious because all cells of factor-producing cultures finally die in the typical manner that is observed when mammalian cells are treated with genuine cyplasin isolated from the mucus of *A. punctata*. Since only a fraction of cells in such cultures is transfected it follows that the cytotoxic factor must be released from the producer cells with the consequence of cell death of producer and non-producer cells. The release of the cytotoxic factor is well in agreement with the predicted secretory signal at the amino terminus of the cDNA-derived amino acid sequence (FIG. 2).

Although this self-destructing system is not suitable to produce significant amounts of biologically active recombinants it reveals the validity of the cDNA cloning approach and it indicates that the factor encoded by the cDNA with the longer insert shows the cyplasin-typical characteristics.

EXAMPLE 6

Recombinant Expression of Bioactive Cyplasin-L and Cyplasin-L-EGFP in Insect Cells Insect cells (e.g. Sf9) are known to be able to perform posttranslational modifications similar to mammalian cells. Since Sf9 cells proved to be much less sensitive to genuine cyplasin preparations (not shown) they are especially suited to generate recombinant cyplasin in sufficient amounts for biological tests. Transfection of SF9 cells with pIZ vector-driven constructs specifying the expression of cyplasin-L or of EGFP-tagged cyplasin-L could not influence the proliferation rate of SF9 cells. Moreover, the spent medium of SF9 cells transfected with the construct specifying cyplasin-L contained significant cytotoxic activity for mammalian cell cultures, which shows that the secretory signal of cyplasin-L is also functioning in insect cells.

In contrast, no cytotoxic factor was released from SF9 cells transfected with the construct specifying EGFP-tagged cyplasin-L. The cyplasin-L-EGFP fusion protein is clearly expressed in SF9 cells, as shown, by EGFP-dependent fluorescence (FIG. 3), but no significant amounts of the cytotoxic factor can be detected in the spent medium of spinner cultures. Interestingly, the Western blot shown in FIG. 4 points to the deletion of the signal sequence in the cyplasin-L section of the fusion protein. This cleavage must occur in such a way that the truncated fusion protein remains cytosolic. Alternatively, retrograde translocation from the ER to the cytosol has to be assumed. Such retrograde translocations have been observed in other systems before [13, 14, 15, 16].

However, the cytotoxic activity of the recombinantly expressed truncated cyplasin-L is maintained when fused to EGFP. The high-speed supernatant of homogenized cyplasin-L-EGFP-expressing SF9 cells was found to contain the factor that is cytotoxic to cultured mammalian cells. Consequently, stably transfected cyplasin-L-EGFP expressing Sf9 cell lines were generated by fluorescence activated cell sorting (FACS), and fractions of the high-speed supernatants of such cultures contained the cyplasin-L-EGFP fusion protein (FIG. 4) and exhibited the biological activities shown in FIG. 5.

EXAMPLE 7

Characteristic Features of Cyplasin-dependent Cytotoxicity

Proliferating mammalian cells exhibit characteristic time and concentration-dependent morphological changes when treated with the biochemically isolated genuine cyplasin from the mucus of *A. punctata* (FIG. 5). The cytotoxic effects of the genuine cyplasin become visible, e.g. in PtK cells, in less than one hour at 50 nM. For this cell line the minimum cytotoxic cyplasin concentration is in the order of 2 nM, however, at this concentration the cytotoxic effects appear foremost after 24 hours. Once induced, the cyplasin effect is irreversible and cell death is observed even if cyplasin-containing medium is replaced by fresh medium. Other cultured mammalian cells show somewhat lower (human skin fibroblasts) or even higher sensitivity (human melanoma cells, glia cells) (FIG. 5).

The morphology of cyplasin-induced cell death is specific. The cells detach from the substratum, they shrink and disjoin from each other if grown as monolayer or in clusters, and occasionally they exhibit numerous small plasma vacuoles. Morphological changes of this type can also be observed in cells undergoing apoptotic cell death, however, typical indicators for apoptosis including nuclear fragmentation and exposure of phosphatidylserine on the outer membrane are missing (FIG. 6).

Moreover, cyplasin exerts its cytotoxic effects only on cells in interphase. Mitotic cells are still able to complete anaphase and cytokinesis at a time when most interphase cells in the same culture already show the cyplasin-typical change in morphology (FIG. 7). However, following completion of mitosis these cells also die when reentering the interphase. Neither cell permeability nor the microtubular cytoskeleton nor intracellular $Ca^{2+}$-levels are affected by cyplasin (not shown).

EXAMPLE 8

Evaluation of the Bioactive Recombinant Cyplasin-L-EGFP

A thorough side-by-side comparison of the biochemically isolated genuine cyplasin and the recombinant cyplasin-L-EGFP version meets the problem that the recombinant is, at present, only available on the level of enriched extracts. Although an exact quantitation is missing so far it is evident that the cyplasin-L-EGFP extracted from stably transfected SF9 cells exhibits cytotoxic activity which is very similar to that induced by the biochemically isolated genuine cyplasin. FIG. 5 presents side by side the effects of genuine cyplasin and recombinant cyplasin-L-EGFP on four different cell lines with established different sensitivities to genuine cyplasin. Using constant amounts of extracts from cyplasin-L-EGFP expressing SF9 cells it is obvious that human skin fibroblasts (HSF) are relatively insensitive to recombinant cyplasin-L-EGFP which holds true also for the biochemically isolated genuine cyplasin. These cells only show a slight initial retraction and a weak tendency to shrink when treated either with genuine cyplasin (50 nM) or with the standard extracts containing the cyplasin-L-EGFP. Finally, they recover and continue to proliferate. Death of HSF cells is only observed at cyplasin concentrations in the order of 100 nM (not shown). In contrast, cells derived from a biopsy of a human melanoma exhibit significantly higher sensitivity when incubated with genuine cyplasin (20 nM), and with the standard extract. Melanoma cells treated either with the genuine cyplasin or with the recombinant cyplasin-L-EGFP show the typical cyplasin-induced retractions, the formation of vacuoles, and finally cell death. Other panels of this figure show glia cells from an established cell line derived from rat embryo cortices. These cells exhibit the highest cyplasin sensitivity of all cells studied so far. The typical cyplasin effect is observed at a concentration that is as low as 0.2 nM, and complete cell death is observed within a five hours observation period. The cells of the rat kangaroo line PtK are irreversibly damaged within 5 hours by incubation with 2 nM genuine cyplasin after five hours. A similar effect is observed after treatment with the standard extract., Prominent plasma vacuolisation and membrane changes are induced in these cells by genuine cyplasin as well as by recombinant cyplasin-L-EGFP.

Summarizing, these results show that the molecular cloning approach released a cDNA encoding a factor exhibiting cytotoxic activity similar to that detected in the secreted mucus of *A. punctata,* and that the cytotoxic effect of the recombinant protein is not obliterated by its fusion to EGFP.

EXAMPLE 9

Target Site for Cyplasin Action

The exact mechanisms behind the cytotoxic effects of cyplasin and recombinant cyplasin are not yet elaborated. However, it is unlikely that the cells take up a protein of this size with the consequence of exerting negative intracellular influence. Long-term observations of cyplasin-treated cells indicate that the first signs of cytotoxic action occur at the outer cellular membrane, at a time when the internal cell morphology shows no anomalies. This observation suggests that cyplasin-docking to the outer cellular membrane represents the trigger for a still unknown cascade of events that finally leads to cell death. This view is also in agreement with other observations. Mammalian cells transfected with expression constructs specifying cyplasin L or EGFP-tagged cyplasin L initially survive and they are able to produce the cytotoxic factor. However, they begin to exhibit the changed morphology as soon as the cytotoxic factor becomes detectable in the spent medium. This suggests that extracellular cyplasin is cytotoxic while intracellular cyplasin is rather non-toxic. Finally, mammalian cells treated with the cyplasin-L-EGFP fusion protein extracted from stably transfected SF9 cells become surrounded by a faint halo of fluorescent fusion protein which is followed by the characteristic retraction and shrinking.

EXAMPLE 10

Absence of In Vivo Toxicity of Cyplasin

In order to test if cyplasin showed cytotoxic effects also in vivo, either genuine or recombinant cyplasin was injected into three groups of mice. Group 1 consisted of 12 DBA2 mice, which were injected with a high concentration of cyplasin into the tail vein. The concentration used exceeded by far the concentration found to be toxic in vitro. Nevertheless, all mice survived, at least up to four weeks. The same result was obtained when in a second group 12 DBA2 mice were injected subcutaneously under identical conditions. They survived and no negative effects were found during the observation period. Finally, a third group (6 mice) was injected into the tail vein using the recombinant cyplasin. Again all mice survived.

EXAMPLE 11

Recombinant Production of Cyplasin without Secretrory Leader Sequence in HeLa Cells Cyplasin is cytotoxic for the host cells if secreted. Thus, it was investigated whether this problem can be overcome by using for recombinant production of cyplasin in human cells a DNA encoding cyplasin without secretory signal sequence. The amino acid sequence of cyplasin (FIG. 2) was analysed using the "signal P program" [19-22]. Two potential cleavage sites for signal-sequences were found in the N-terminal part of the amino acid sequence which characterize cyplasin as a secreted protein (see FIG. 10). The putative cleavage site is between aa positions 19 and 20 (highest probability) or 52 and 53 (lower probability). In order to ensure removal of the complete signal peptide, the DNA sequence encoding the signal peptide from aa position 1 to 52 was removed from the insert of the cyplasin encoding plasmid described in Example 1. (F,G), above. The modified DNA sequence comprising the EGFP-tag was cloned in appropriate sites of the pcDNA3-vector resulting in the corresponding cyplasin-L-(Sig-Seq.)-EGFP expression construct. Then HeLa-cells were transfected with this construct. In order to allow identification of transformed cells this construct was additionally capable of expressing the gene encoding the green fluorescent protein (GFP) as a marker. After selecting correctly transformed cells by use of the antibiotic G418-sulfate and after culturing the transfected cells for some weeks for selecting transformants with the vector stably integrated into their genome, a single cell cloning was carried out. As shown in FIG. 12, the stably transfected cells express cyplasin. Cyplasin was isolated as described in Example 1 (J,K) and it could be shown by using the methods described in Example 1 (C,D) that it exhibits the same cytotoxic activity as the native cyplasin isolated from *Aplysia punctata*.

A plasmid [pcDNA3-Cytoplasin.Mut-(-Sig.Seq.)-EGFP] containing the coding sequence for cyplasin without a signal sequence has been deposited under Budapest Treaty with the DSMZ (Deutsche Sammlung von Mikroorganismen und Zellkulturen Gmbh, Mascheroder Weg 2, Braunschweig, Germany) on Aug. 22, 2002 under DSM 15153.

REFERENCES 1. de-Vries D J and Beart P M (1995). Fishing for drugs from the sea: status and strategies. *Trends in Pharmacol. Sci.* 16, 275-279.
2. Wallace R W (1997). Drugs from the sea: harvesting the results of aeons of chemical evolution. *Mol. Med. Today* 3, 291-295.
3. Fenical W (1997). New pharmaceuticals from marine organisms. *Trends Biotechnol.* 15, 339-341.
4. Chalfie M, Tu Y, Euskirchen G, Ward W W, and Prasher D C. (1994). Green fluorescent protein as a marker for gene expression. *Science* 263, 802-805.
5. Yamazaki M (1993). Antitumor and antimicrobial glycoproteins from sea hares. *Comp. Biochem. Physiol. C.* 105, 141-146.
6. Iijma R, Kisugi J, and Yamazaki M (1994). Biopolymers from marine invertebrates. XIV. Antifungal property of Dolabellanin A, a putative self-defense molecule of the sea hare, *Dolabella auricularia*. *Biol. Pharm. Bull.* 17, 1144-1146.
7. Obara K, Otsuka-Fuchino H, Sattayasai N, Nonomura Y, Tsuchiya T, Tamiya, T. (1992). Molecular cloning of the antibacterial protein of the giant African snail, *Achatina fulica Ferussac*. *Eur. J. Biochem.* 209, 1-6.
8. Vermes I, Haanen C. Steffens-Nakken H, and Reutelingsperger C (1995). A novel assay for apoptosis: flow cytometric detection of phosphatidylserine expression on early apoptotic cells using fluorescein labelled Annexin V. *J. Immunol. Methods* 184, 39-51.
9. Gescher A (2000). Staurosporine analogues—Pharmacological toys or useful antitumour agents? *Crit. Rev. Oncol. Hematol.* 34, 127-135.
10. Johnson D A, Gautsch J W, Sportsman J R, and Elder J H (1984). Improved technique utilizing nonfat dry milk for analysis of proteins and nucleic acids transferred to nitrocellulose. *Gene Anal. Techniques* 1, 3-8.
11. McGeoch D J (1985). On the predictive recognition of signal peptide sequences. *Virus Res.* 3, 271-286.
12. Takamatsu N, Shiba T, Muramoto K, and Kamiya H (1995). Molecular cloning of the defense factor in the albumen gland of the sea hare *Aplysia kurodai*. *FEBS-Lett.* 377, 373-376.

13. Wang Y, Chen D, and Androlewicz M J (1999). The role of endoplasmic reticulum-associated protein degradation in MHC class I antigen processing. *Immunol. Rev.* 172, 67-72.
14. Wang Y and Androlewicz M J (2000). Oligosaccharide trimming plays a role in the endoplasmatic reticulum-associated degradation of tyrosinase. *Biochem. Biophys. Res. Commun.* 271, 22-27.
15. Karaivanova V K, and Spiro R G (2000). Effect of proteasome inhibitors on the release into the cytosol of free polymannose oligosaccharides from glycoproteins. *Glycobiology* 10, 727-735.
16. Rothbarth K, Kempf T, Juodka B, Glaser T, Stammer H, and Werner D (2001). Intracellular location and nuclear targeting of the Spi-1, Spi-2 and Spi-3 gene-derived serine protease inhibitors in non-secretory cells. *Eur. J. Cell Biol.* 80, 341-348.
17. Sperandio S, de Belle I, and Bredesen D E (2000). An alternativ, nonapoptotic form of programmed cell death. *Proc. Natl. Acad. Sci. USA* 97, 14376-14381.
18. Hanahan D and Weinberg R A (2000). The hallmarks of cancer. *Cell* 100, 57-70.
19. Nielsen H, Engelbrecht J, Brunak S and von Heijne G (1997). Identification of prokaryotic and eukaryotic signal peptides and prediction of their cleavage sites. *Protein Engineering* 10, 1-6.
20. Nielsen H, Brunak S and von Heijne G (1999). Review. Machine learning approaches to the prediction of signal peptides and other protein sorting signals. *Protein Engineering* 12, 3-9.
21. Nielsen H, Engelbrecht J, Brunak S and von Heijne G (1997). A neural network method for identification of prokaryotic and eukaryotic signal peptides and predicition of their cleavage sites. *Int. J. Neural. Sys.* 8, 581-599.
22. Nielsen H (May 25, 1999). From sequence to sorting: Prediction of signal peptides. Ph.D.thesis. Defended at Department of Biochemistry, Stockholm University, Sweden.

The invention claimed is:

1. An isolated protein encoded by a nucleic acid molecule selected from the group consisting of:
   a) a nucleic acid molecule encoding a protein comprising the amino acid sequence from position 20 or 53 to 558 of SEQ ID NO: 1;
   b) a nucleic acid molecule comprising the sequence of SEQ ID NO: 5; and
   c) a nucleic acid molecule, the sequence of which deviates from the nucleic acid sequences specified in (a) or (b) due to the degeneration of the genetic code,
   wherein said protein lacks a functional secretory signal sequence.

2. A pharmaceutical composition comprising a protein of claim 1.

3. The pharmaceutical composition according to claim 2, wherein the composition is used for treating cancer.

4. The protein of claim 1, wherein the protein is cyplasin with a deleted or non-functional signal sequence.

5. The protein of claim 1, wherein the protein exhibits biological properties of cyplasin.

* * * * *

SEQUENCE LISTING

<160> NUMBER OF SEQ ID NOS: 5

<210> SEQ ID NO 1
<211> LENGTH: 558
<212> TYPE: PRT
<213> ORGANISM: Aplysia punctata

<400> SEQUENCE: 1

```
Met Ala Val Arg Phe Leu Ala Pro Gly Leu Leu Thr Leu Ala Thr Leu
1               5                   10                  15

Val Ser Gly Arg Thr Val Cys Glu Ser Lys Gln Glu Cys Asp Ala Ala
            20                  25                  30

Gln Cys Asp Lys Thr Leu Asp Val Ala Ile Val Gly Ala Gly Ala Ala
        35                  40                  45

Gly Ala Tyr Ser Ala Tyr Leu Arg Asn Lys Gly Gln Asn Ile Gly
    50                  55                  60

Val Phe Glu Phe Cys Asp Arg Val Gly Gly Arg Leu Phe Thr Tyr Gln
65                  70                  75                  80

Leu Pro Asn Thr Pro Asp Val Gln Leu Glu Leu Gly Gly Met Arg Tyr
                85                  90                  95

Ile Thr Gly Ala His Asn Leu Leu Glu Gly Val Val Arg Gln Leu Gly
            100                 105                 110

Leu Thr Pro Val Val Phe Thr Glu Gly Phe Gly Lys Leu Gly Arg Thr
        115                 120                 125

Arg Tyr Tyr Leu Arg Gly Gln Ser Leu Thr Phe Gln Glu Val Leu Thr
    130                 135                 140

Gly Asp Val Pro Tyr Asn Leu Thr Val Ala Glu Lys Gln Asn Gln Asp
145                 150                 155                 160

Asn Ile Phe Ala Phe Tyr Leu Lys Glu Leu Thr Arg Phe Asp Val Gly
                165                 170                 175

Asp Gly Phe Val Thr Arg Glu Gln Leu Leu Lys Leu Arg Val Ser Asp
            180                 185                 190

Gly Arg Leu Leu Tyr Gln Leu Thr Phe Asp Glu Ala Leu Asp Leu Val
        195                 200                 205

Ala Ser Pro Glu Gly Lys Glu Phe Ala Arg Asp Ile His Val Phe Thr
    210                 215                 220
```

```
Thr Glu Val Ser Asp Asp Ala Asn Ala Val Ser Val Phe Asp Asp His
225                 230                 235                 240

Leu Gly Glu Asp Gly Val Gly Glu Glu Ile His Thr Val Gln Glu Gly
            245                 250                 255

Met Gln Lys Val Pro Glu Gln Leu Leu Arg Ala Phe Gly Asn Ser Ser
            260                 265                 270

Val Phe Gly His Arg Val Phe Thr Asn Leu Gln Leu Lys Ala Ile Arg
        275                 280                 285

Ser Lys Ser Asp Lys Ser His Val Leu Tyr Phe Arg Thr Thr Ser Thr
290                 295                 300

Val Asp Gly Lys Thr Thr Ile Leu Lys Phe Glu Pro Leu Gln Lys Val
305                 310                 315                 320

Cys Thr Arg Gln Ile Ile Leu Ala Leu Pro Val Phe Ala Leu Met Gln
                325                 330                 335

Val Asp Trp Pro Pro Leu Arg Glu Asn Arg Ala Gln Lys Ala Tyr Gly
            340                 345                 350

Ala Val Arg Thr Ile Pro Ala Ser Lys Val Phe Met Thr Phe Asp Gln
        355                 360                 365

Pro Trp Trp Leu Gln Asn Asp Val Thr Asp Phe Pro Ala Phe Val Thr
370                 375                 380

Lys Gly Asp Thr Thr Phe Ser Gln Met Tyr Asp Trp Lys Lys Ser Glu
385                 390                 395                 400

Ala Ser Gly Asp Tyr Ile Leu Ile Ala Ser Tyr Ala Asp Gly Asn Asn
                405                 410                 415

Thr Leu Phe Gln Arg Val Leu Arg Asp Gln Gly Glu Pro Ile Asn Gly
            420                 425                 430

Ser Glu Ala Gly Ala His Ile Val Ser Glu Pro Leu Lys Asn Gln Ile
        435                 440                 445

Leu Asp His Leu Ala Asp Ala Phe Gly Val Pro Arg Ser Asp Ile Gln
450                 455                 460

Glu Pro Lys Thr Ala Val Ser Lys Phe Trp Thr Asp Tyr Pro Phe Gly
465                 470                 475                 480

Cys Gly Trp Ile Thr Trp Arg Ala Gly Tyr His Phe Asp Asp Val Met
                485                 490                 495

Asn Thr Met Arg Arg Pro Ser Leu Thr Asp Glu Val Tyr Val Val Gly
            500                 505                 510

Ala Asp Tyr Ser Trp Gly Leu Ile Ser Ser Trp Val Glu Gly Ala Leu
        515                 520                 525

Glu Thr Ser Tyr Glu Val Ile Asp Thr Tyr Phe Lys Ser Glu Arg Ser
530                 535                 540

His Asn Val Gln Pro Pro Ser His Met Ala Ser His Val Gly
545                 550                 555

<210> SEQ ID NO 2
<211> LENGTH: 421
<212> TYPE: PRT
<213> ORGANISM: Aplysia punctata

<400> SEQUENCE: 2

Met Ala Val Arg Phe Leu Ala Pro Gly Leu Leu Thr Leu Ala Thr Leu
1               5                   10                  15

Val Ser Gly Arg Thr Val Cys Glu Ser Lys Gln Glu Cys Asp Ala Ala
            20                  25                  30

Gln Cys Asp Lys Thr Leu Asp Val Ala Ile Val Gly Ala Gly Ala Ala
```

```
                    35                  40                  45
Gly Ala Tyr Ser Ala Tyr Leu Leu Arg Asn Lys Gly Gln Asn Ile Gly
         50                  55                  60

Val Phe Glu Phe Cys Asp Arg Val Gly Gly Arg Leu Phe Thr Tyr Gln
 65                  70                  75                  80

Leu Pro Asn Thr Pro Asp Val Gln Leu Glu Leu Gly Gly Met Arg Tyr
                 85                  90                  95

Ile Thr Gly Ala His Asn Leu Leu Glu Gly Val Val Arg Gln Leu Gly
             100                 105                 110

Leu Thr Pro Val Val Phe Thr Glu Gly Phe Gly Lys Leu Gly Arg Thr
         115                 120                 125

Arg Tyr Tyr Pro Arg Gly Gln Ser Leu Thr Phe Gln Glu Ala Leu Thr
     130                 135                 140

Gly Asp Val Pro Tyr Asn Leu Thr Val Ala Glu Lys Gln Asn Gln Asp
145                 150                 155                 160

Asn Ile Phe Ala Phe Tyr Leu Lys Glu Leu Thr Arg Phe Asp Val Gly
                 165                 170                 175

Asp Gly Phe Val Thr Arg Glu Gln Leu Leu Lys Leu Arg Ala Ser Asp
             180                 185                 190

Gly Arg Pro Leu Tyr Gln Leu Thr Phe Asp Glu Ala Leu Asp Leu Val
         195                 200                 205

Ala Ser Pro Glu Gly Lys Glu Phe Ala Arg Asp Ile His Val Phe Thr
     210                 215                 220

Thr Glu Val Ser Asp Ala Asn Ala Val Ser Val Phe Asp His
225                 230                 235                 240

Leu Gly Glu Asp Gly Val Gly Glu Glu Ile His Thr Val Gln Glu Gly
                 245                 250                 255

Met Gln Lys Val Pro Glu Gln Pro Leu Arg Ala Phe Gly Asn Ser Ser
             260                 265                 270

Val Phe Gly His Arg Val Phe Thr Asn Leu Gln Leu Lys Ala Ile Arg
         275                 280                 285

Ala Lys Ser Asp Lys Ser His Val Pro Tyr Phe Arg Pro Thr Ser Thr
     290                 295                 300

Val Asp Gly Lys Thr Thr Ile Leu Lys Phe Glu Pro Leu Gln Lys Val
305                 310                 315                 320

Cys Ala Arg Gln Ile Ile Leu Ala Leu Pro Val Phe Ala Leu Met Gln
                 325                 330                 335

Val Asp Trp Pro Pro Leu Arg Glu Asn Arg Ala Gln Lys Ala Tyr Gly
             340                 345                 350

Ala Val Arg Thr Ile Pro Ala Ser Lys Val Phe Met Thr Phe Asp Gln
         355                 360                 365

Pro Trp Trp Leu Gln Asn Asp Val Thr Asp Phe Pro Ala Phe Val Thr
     370                 375                 380

Lys Gly Asp Thr Thr Phe Ser Gln Met Tyr Asp Trp Lys Lys Pro Asn
385                 390                 395                 400

Val Ser Gly Asp Tyr Ile Leu Ile Ala Ser Tyr Ala Asp Gly Ser Thr
                 405                 410                 415

Gln Pro Trp Ile His
             420

<210> SEQ ID NO 3
<211> LENGTH: 506
<212> TYPE: PRT
<213> ORGANISM: Artificial Sequence
```

```
<220> FEATURE:
<223> OTHER INFORMATION: Synthetic Construct

<400> SEQUENCE: 3

Ala Tyr Leu Leu Arg Asn Lys Gly Gln Asn Ile Gly Val Phe Glu Phe
1               5                   10                  15

Cys Asp Arg Val Gly Gly Arg Leu Phe Thr Tyr Gln Leu Pro Asn Thr
            20                  25                  30

Pro Asp Val Gln Leu Glu Leu Gly Gly Met Arg Tyr Ile Thr Gly Ala
        35                  40                  45

His Asn Leu Leu Glu Gly Val Val Arg Gln Leu Gly Leu Thr Pro Val
50                  55                  60

Val Phe Thr Glu Gly Phe Gly Lys Leu Gly Arg Thr Arg Tyr Tyr Leu
65                  70                  75                  80

Arg Gly Gln Ser Leu Thr Phe Gln Glu Val Leu Thr Gly Asp Val Pro
                85                  90                  95

Tyr Asn Leu Thr Val Ala Glu Lys Gln Asn Gln Asp Asn Ile Phe Ala
            100                 105                 110

Phe Tyr Leu Lys Glu Leu Thr Arg Phe Asp Val Gly Asp Gly Phe Val
        115                 120                 125

Thr Arg Glu Gln Leu Leu Lys Leu Arg Val Ser Asp Gly Arg Leu Leu
    130                 135                 140

Tyr Gln Leu Thr Phe Asp Glu Ala Leu Asp Leu Val Ala Ser Pro Glu
145                 150                 155                 160

Gly Lys Glu Phe Ala Arg Asp Ile His Val Phe Thr Thr Glu Val Ser
                165                 170                 175

Asp Asp Ala Asn Ala Val Ser Val Phe Asp His Leu Gly Glu Asp
            180                 185                 190

Gly Val Gly Glu Glu Ile His Thr Val Gln Glu Gly Met Gln Lys Val
                195                 200                 205

Pro Glu Gln Leu Leu Arg Ala Phe Gly Asn Ser Ser Val Phe Gly His
        210                 215                 220

Arg Val Phe Thr Asn Leu Gln Leu Lys Ala Ile Arg Ser Lys Ser Asp
225                 230                 235                 240

Lys Ser His Val Leu Tyr Phe Arg Thr Thr Ser Thr Val Asp Gly Lys
                245                 250                 255

Thr Thr Ile Leu Lys Phe Glu Pro Leu Gln Lys Val Cys Thr Arg Gln
            260                 265                 270

Ile Ile Leu Ala Leu Pro Val Phe Ala Leu Met Gln Val Asp Trp Pro
        275                 280                 285

Pro Leu Arg Glu Asn Arg Ala Gln Lys Ala Tyr Gly Ala Val Arg Thr
    290                 295                 300

Ile Pro Ala Ser Lys Val Phe Met Thr Phe Asp Gln Pro Trp Trp Leu
305                 310                 315                 320

Gln Asn Asp Val Thr Asp Phe Pro Ala Phe Val Thr Lys Gly Asp Thr
                325                 330                 335

Thr Phe Ser Gln Met Tyr Asp Trp Lys Lys Ser Glu Ala Ser Gly Asp
            340                 345                 350

Tyr Ile Leu Ile Ala Ser Tyr Ala Asp Gly Asn Asn Thr Leu Phe Gln
        355                 360                 365

Arg Val Leu Arg Asp Gln Gly Glu Pro Ile Asn Gly Ser Glu Ala Gly
    370                 375                 380

Ala His Ile Val Ser Glu Pro Leu Lys Asn Gln Ile Leu Asp His Leu
385                 390                 395                 400
```

```
Ala Asp Ala Phe Gly Val Pro Arg Ser Asp Ile Gln Glu Pro Lys Thr
            405                 410                 415

Ala Val Ser Lys Phe Trp Thr Asp Tyr Pro Phe Gly Cys Gly Trp Ile
            420                 425                 430

Thr Trp Arg Ala Gly Tyr His Phe Asp Asp Val Met Asn Thr Met Arg
        435                 440                 445

Arg Pro Ser Leu Thr Asp Glu Val Tyr Val Gly Ala Asp Tyr Ser
    450                 455                 460

Trp Gly Leu Ile Ser Ser Trp Val Glu Gly Ala Leu Glu Thr Ser Tyr
465                 470                 475                 480

Glu Val Ile Asp Thr Tyr Phe Lys Ser Glu Arg Ser His Asn Val Gln
                485                 490                 495

Pro Pro Ser His Met Ala Ser His Val Gly
            500                 505

<210> SEQ ID NO 4
<211> LENGTH: 12
<212> TYPE: PRT
<213> ORGANISM: Artificial Sequence
<220> FEATURE:
<223> OTHER INFORMATION: Synthetic construct

<400> SEQUENCE: 4

Ser Gly Asp Tyr Ile Leu Ile Ala Ser Tyr Ala Asp
1               5                   10

<210> SEQ ID NO 5
<211> LENGTH: 1518
<212> TYPE: DNA
<213> ORGANISM: Aplysia punctata

<400> SEQUENCE: 5
gcctaccttt tgaggaataa aggtcagaac atcggggtct tcgaattctg tgacagagtg      60
ggtggtcggc tgttcaccta tcagttgcct aataccccg acgtgcagct ggaactgggc     120
gggatgcggt acatcaccgg cgctcataac ctgctcgagg gagtcgttcg tcagctggga     180
ctgaccccag tagtgtttac agaaggcttc ggtaagctgg ccgtacacg ctattacctg     240 aggggacagt ccctgacctt ccaggaagtg ctgacaggcg acgtgccata caaccttacc     300
gtcgcggaga agcagaacca ggacaatatt ttcgccttct atctcaagga actaacccgt     360
ttcgacgtag cgacggtttc gtgaccaga gaacaactgc tgaaactgcg cgtcagcgat      420
gggaggctcc tctaccaact gacgttcgac gaagccctgg acctggtagc atcgccggaa     480
ggtaaagaat tgccaggga cattcacgtg tttacgacgg aggtttcaga cgacgccaac     540
gcggtttcgg tgttcgacga cgacttaggt gaggacggcg taggcgagga gatccatacc     600
gtgcaagaag gaatgcagaa agtaccggag caactgctgc gtgcatttgg aaacagttcc     660
gtcttcggcc acagggtctt cactaacctg caactgaaag caattcgaag caaatccgac     720
aagagccacg tcctgtactt taggaccacc tccacggttg acggcaaaac aacaattctc     780
aaattcgagc cgctgcagaa ggtctgcacg cgtcagatta tcctagctct gcctgtgttc     840
gccctcatgc aggtcgattg gcctcccctg cgtgagaatc gggcgcagaa ggcgtacggc     900
gcggtcagga ccattccagc gagcaaggtc ttcatgacgt tcgaccaacc gtggtggctt     960
cagaacgatg tgacagactt cccagcgttt gtgaccaaag agacaccac tttctcgcaa    1020 atgtacgact ggaaaaagtc cgaggcttct ggtgactaca tcctcatcgc ttcgtacgcc    1080
```

-continued

```
gacggcaaca ataccctctt ccagagggtg ctgcgcgacc aagggagcc gatcaacggc     1140 agtgaagccg gcgcccacat cgtgtccgag ccccttaaga accaaatttt ggaccacctc    1200
gcggacgcgt ttggcgtccc ccgttcggac attcaggagc ccaaaacggc ggtcagcaag    1260
ttttggactg actaccccgtt tgggtgtgga tggattacat ggcgggccgg ctaccacttc   1320
gacgatgtga tgaacaccat gcgcagaccc tcactcaccg acgaggtcta cgttgtgggt   1380
gcggactact cttggggcct tatttcttcc tgggtggaag gcgccctgga aacctcctac    1440
gaggtaatcg atacatactt caaaagcgag cggtcacata atgtgcaacc tccaagccac    1500
atggcctccc acgtgggc                                                  1518
```